United States Patent [19]
Crawford et al.

[11] Patent Number: 5,753,595
[45] Date of Patent: May 19, 1998

[54] HERBICIDAL 3-(SUBSTITUTED BENZOXAZOL-7-YL) AND 3-(SUBSTITUTED BENZOTHIAZOL-7-YL)-1-SUBSTITUTED-6-TRIFLUOROMETHYL-2 4-(1H 3H) PYRIMIDINEDIONES

[75] Inventors: Scott D. Crawford, Bordentown; Lester L. Maravetz, Westfield; George Theodoridis, Princeton, all of N.J.

[73] Assignee: FMC Corporation, Philadelphia, Pa.

[21] Appl. No.: 743,973

[22] Filed: Jul. 31, 1996

Related U.S. Application Data

[60] Provisional application No. 60/003,080, Aug. 31, 1995.
[51] Int. Cl.$^6$ .......................... E07D 239/54; A01N 43/54
[52] U.S. Cl. .......................... 504/243; 544/310
[58] Field of Search .......................... 504/243; 544/310

[56] References Cited

U.S. PATENT DOCUMENTS

| | | | |
|---|---|---|---|
| 5,521,147 | 5/1996 | Theodoridis | 504/243 |
| 5,661,108 | 8/1997 | Crawford et al. | 504/243 |

*Primary Examiner*—John M. Ford
*Attorney, Agent, or Firm*—H. Robinson Ertelt; I. Robert Silverman

[57] ABSTRACT

Herbicidal 3-(substituted benzoxazol-7-yl) and 3-(substituted benzothiazol-7-yl)-1-substituted-6-trifluoromethyl-2,4-(1H,3H)pyrimidinediones, compositions containing them, and methods of using them to control undesired plant growth are disclosed, as are novel intermediates used in the preparation of these compounds. The herbicidal compounds of the present invention are defined by the following generic structure:

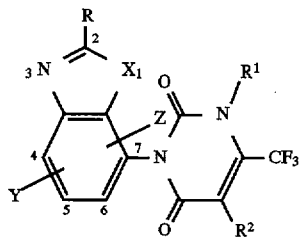

in which R is selected from a variety of substituents, including halogen, alkyl, alkenyl, alkynyl, phenyl, phenylalkyl, alkylphenylalkyl, haloalkyl, hydroxy, alkoxy, hydroxyalkyl, halophenyl, halophenylalkyl, alkoxyphenyl, sulfhydryl, alkylthio, piperidinyl, alkylamino, alkoxyalkyl, phenoxy, amino, alkylsulfonylamino, phenylsulfonylamino, and carboxy; $R^1$ is alkyl or amino; $R^2$ is hydrogen or halogen; X is oxygen or sulfur; Y is hydrogen, halogen, alkoxy, cyano, or nitro, and; Z is halogen; where halogen is bromine, chlorine, fluorine, or iodine, and each alkyl, alkoxy, alkenyl, or alkynyl moiety has one to six carbon atoms.

19 Claims, No Drawings

HERBICIDAL 3-(SUBSTITUTED BENZOXAZOL-7-YL) AND 3-(SUBSTITUTED BENZOTHIAZOL-7-YL)-1-SUBSTITUTED-6-TRIFLUOROMETHYL-2 4-(1H 3H) PYRIMIDINEDIONES

This application claims benefit of provisional application Ser. No. 60/003,080, filed Aug. 31, 1995.

The invention described in this application pertains to weed control in agriculture, horticulture, and other fields where there is a desire to control unwanted plant growth. More specifically, the present application describes certain herbicidal 3-(substituted benzoxazol-7-yl) and 3-(substituted benzothiazol-7-yl)-1-substituted-6-trifluoromethyl-2,4-(1H,3H)pyrimidinediones, as well as compositions containing them, methods of preparing them, and methods for preventing or destroying undesired plant growth by preemergence or postemergence application of herbicidal compositions to the locus where control is desired. The herbicidal activity of the present compounds has not previously been described.

It has now been found that certain 3-(substituted benzoxazol-7-yl) and 3-(substituted benzothiazol-7-yl)-1-substituted-6-trifluoromethyl-2,4-(1H,3H)-pyrimidinediones are highly active herbicides. The novel compounds of the present invention are defined by the following generic structure:

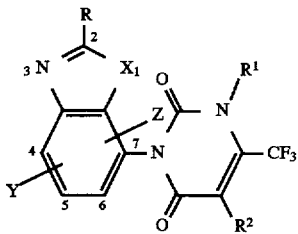

wherein:

R is halogen, straight or branched chain alkyl, alkenyl, alkynyl, phenyl, phenylalkyl, alkylphenylalkyl, haloalkyl, hydroxy, alkoxy, hydroxyalkyl, halophenyl, halophenylalkyl, alkoxyphenyl, sulfhydryl, alkylthio, piperidinyl, alkylamino, alkoxyalkyl, phenoxy, amino, alkylsulfonylamino, phenylsulfonylamino, carboxy, propionyl, halopropionyl, allyloxy, propargyloxy, acetylamino, alkylthienyl, alkoxyarylalkyl, alkylsulfinyl, alkylsulfonyl, acetoxyalkyl, alkylcarbonyldioxyalkyl, alkylaminosulfonylamino, haloalkylsulfonylamino, arylaminosulfonylamino, N-alkylsulfonyl-N-alkylamino, N-alkylsulfony-N-alkoxyalkylamino, N-alkylsulfonyl-N-alkynylamino, N-alkylsulfonyl-N-alkenylamino, N-phenylsulfonyl-N-alkylamino, acetoxyalkylamino, acetoxy, sodium carboxylato, amino-carboxylato, alkylcarbamoyl, alkylsulfonylcarbamoyl, alkoxycarbonyl, acetoxyhaloalkyl, acetoxyalkenyl, acetoxyhaloalkenyl, acetoxyalkoxy, alkenyloxy, alkynyloxy, acetoxyalkylthio, cyanoalkylthio, alkynylthio, phenylalkylthio, acetoxyalkylthioalkyl, phenylalkylthioalkyl, alkylsulfonylaminoalkyl, alkoxyphosphinyloxyamino, N-acetyl-N-alkylsulfonylamino, alkynyloxyalkyl, alkylcarboxylatophenoxy, halophenoxy, alkylphenoxy, alkoxypropionyloxyphenoxy, or haloalkoxypropionyl;

$R^1$ is alkyl or amino;

$R^2$ is hydrogen or halogen;

X is oxygen or sulfur;

Y is hydrogen, halogen, alkoxy, cyano, or nitro, and;

Z is halogen;

where halogen is bromine, chlorine, fluorine, or iodine, and each alkyl, alkoxy, alkenyl or alkynyl moiety, alone or in a combined term has one to six carbon atoms.

Preferred compounds are those in which R is alkyl, haloalkyl, piperidinyl, alkylamino, and alkoxyalkyl; $R^1$ is methyl or amino; $R^2$ is hydrogen or chlorine, X is oxygen or sulfur, Y is hydrogen, 4-chloro, 4-bromo, or 4-nitro; and Z is 6-chloro when Y is hydrogen or 6-fluoro when Y is other than hydrogen, where each alkyl moiety has one to four carbon atoms.

The compounds of the present invention were prepared by methods known to one skilled in the art.

In general the 3-(substituted-benzoxazol-7-yl)-1-substituted-6-trifluoromethyl-2,4-(1H,3H)-pyrimidinedione compounds were prepared by one of two routes, depending on whether the benzoxazole ring was formed prior to or after the formation of the 2,4-(1H,3H)-pyrimidinedione ring.

As depicted in Schema 1, those compounds in which the benzoxazole ring was formed prior to the formation of the 2,4-(1H,3H)-pyrimidinedione ring were prepared from one of two starting materials. The first starting material used to prepared those compounds in which the benzoxazole ring is formed first is an hydroxy-, alkyl hydroxy- or alkyl methylhydroxypropionate (STM1), which is reacted with an alkyl halide, for example methyl iodide, under basic conditions to form the appropriate methoxypropionate (A-1). The propionate (A-1) is in turn hydrogenated under basic conditions to form the corresponding propanoic acid (A-2).

The second starting material used to prepared those compounds in which the benzoxazole ring is formed first is a substituted-3-chloroaniline (STM2). The aniline (STM2) is reacted with the appropriate alkyl anhydride, for example trimethylacetic anhydride, under acidic conditions, yielding the corresponding N-(substituted-3-chlorophenyl)alkylamide (B-1). The aniline (STM2) can also be reacted with the appropriate propanoic acid (A-2), for example 2-methoxy-2-methylpropanoic acid, under basic conditions to form the appropriate N-(substituted-3-chlorophenyl)-substituted-alkylpropion-amide (B-2), for example N-(3-chloro-4-fluorophenyl)-2-methoxy-2-methyl-propionamide. The amides (B-1 or B-2) are in turn treated with n-butyl-lithium and cyclized with solid carbon dioxide, affording the corresponding [2-alkyl- or 2-(substituted-alkyl)-substituted-benzoxazol-7-yl]carboxylic acid (C), for example, (2-t-butyl-6-fluorobenzoxazol-7-yl)carboxylic acid. The so-prepared carboxylic acid (C) is then reacted with ethyl chloroformate, 4-methylmorpholine, and sodium azide, yielding the corresponding [2-alkyl- or 2-(substituted-alkyl)-substituted-benzoxazol-7-yl]carbonyl azide (C-1), which is treated with ethanol to form the corresponding ethyl N-[2-alkyl- or 2-(substituted-alkyl)-substituted-benzoxazol-7-yl] carbamate (D). Additional substituents may optionally be added to the benzoxazole ring at this point. For example, ethyl N-(2-t-butyl-6-fluorobenzoxazol-7-yl)carbamate (D) is treated with N,N-dichlorourethane under acidic conditions, affording ethyl N-(2-t-butyl-4-chloro-6-fluorobenzoxazol-7-yl)carbamate (E). The carbamates D and E are then reacted with ethyl 3-amino-4,4,4-trifluorocrotonate, sodium methoxide, and DBU to form the corresponding 3-[2-alkyl- or 2-(substituted-alkyl)-substituted-benzoxazol-7-yl]-6-trifluoromethyl-2,4-(1H,3H)-pyrimidine-dione (F). The pyrimidinedione (F) is further reacted under basic conditions with an alkyl halide, for example methyl iodide, or O-(2,4-dinitrophenyl)

hydroxylamine, or 1-aminooxysulfonyl-2,4,6-trimethylbenzene, affording the targeted 3-[2-alkyl- or 2-(substituted-alkyl)-substituted-benzoxazol-7-yl]-1-alkyl-6-trifluoromethyl-2,4-(1H,3H)-pyrimidinedione (I) or 3-[2-alkyl- or 2-(substituted-alkyl)-substituted-benzoxazol-7-yl]-1-amino-6-trifluoromethyl-2,4-(1H,3H)-pyrimidinedione (II). Examples 1, 2, 4, and 5 provide the detailed procedures for this route.

At this point additional substituents may be optionally added to the pyrimidinedione ring. For example, a chlorine moiety was added to the 3-(2-t-butyl-4-chlorobenzoxazol-7-yl)-1-methyl-6-trifluoromethyl-2,4-(1H,3H)-pyrimidinedione molecule (I) by treating it with N,N-dichlorourethane under acidic conditions, affording 3-(2-t-butyl-4-chlorobenzoxazol-7-yl)-1-methyl-5-chloro-6-trifluoromethyl-2,4-(1H,3H)-pyrimidinedione (III). In addition, the 3-[2-(substituted-methoxyalkyl)-substituted-benzoxazol-7-yl]-1-alkyl-6-trifluoromethyl-2,4-(1H,3H)-pyrimidinedione (I), for example 3-[2-(1-methoxy-1-methylethyl)-4-chloro-6-fluorobenzoxazol-7-yl)-1-methyl-6-trifluoromethyl-2,4-(1H,3H)-pyrimidinedione, can be hydrogenated under basic conditions, yielding the targeted 3-[2-(substituted-hydroxyalkyl)-substituted-benzoxazol-7-yl]-1-alkyl-6-trifluoromethyl-2,4-(1H,3H)-pyrimidinedione (IV), for example 3-[2-(1-hydroxy-1-methylethyl)-4-chloro-6-fluorobenzoxazol-7-yl)-1-methyl-6-trifluoromethyl-2,4-(1H,3H)-pyrimidinedione. Examples 3 and 15 provide the detailed procedures for these methods.

As depicted in Schema 2, those compounds in which the benzoxazole ring was formed after the formation of the 2,4-(1H,3H)-pyrimidinedione ring were prepared by reacting a disubstituted aniline (STM3), for example 4-chloro-2-fluoroaniline, with N,N-dichlorourethane under acid conditions, yielding the appropriate trisubstituted aniline (AA). The anilines (STM3 or AA) are then reacted with pyridine and ethyl chloroformate, yielding the corresponding ethyl N-(disubstituted-or trisubstituted-phenyl)carbamate (H). When the carbamate (H) is an ethyl N-(disubstituted-2-fluorophenyl)carbamate, for example ethyl N-(4-chloro-2,6-difluorophenyl)carbamate, it is nitrated with nitric acid and sulfuric acid to form the corresponding ethyl N-(disubstituted-2-fluoro-3-nitrophenyl)carbamate (H-1). The ethyl N-(disubstituted-2-fluoro-3-nitrophenyl)carbamate (H-1) is in turn reacted with sodium trimethylsilanoate in the presence of methanol and dioxane to form the ethyl N-(disubstituted-2-methoxy-3-nitrophenyl)carbamate (H-2). The carbamate (H-2) is then reduced with iron powder and hydrochloric acid, yielding the corresponding ethyl N-(disubstituted-3-amino-2-methoxyphenyl)carbamate (H-3).

The ethyl N-(disubstituted-phenyl)carbamate (H) is reacted with ethyl 3-amino-4,4,4-trifluorocrotonate, sodium methoxide, and DBU to form the corresponding 3-(disubstituted-phenyl)-6-trifluoromethyl-2,4-(1H,3H)-pyrimidinedione (I), for example, 3-(4-chloro-2-fluorophenyl)-6-trifluoromethyl-2,4-(1H,3H)-pyrimidinedione. The pyrimidinedione (I) is reacted under basic conditions with an alkyl halide, for example methyl iodide, to form the corresponding 3-(disubstituted-phenyl)-1-alkyl-6-trifluoromethyl-2,4-(1H,3H)-pyrimidinedione (J). The pyrimidinedione (J) is then nitrated with hydrochloric and nitric acid to form the corresponding 3-(2,4-disubstituted-5-nitrophenyl)-1-alkyl-6-trifluoromethyl-2,4-(1H,3H)-pyrimidinedione (K), which is then reduced with iron powder and acetic acid to form the corresponding 3-(5-amino-disubstituted-phenyl)-1-alkyl-6-trifluoromethyl-2,4-(1H,3H)-pyrimidinedione (L). The appropriate carbamate (H-3) is reacted with ethyl 3-amino-4,4,4-trifluorocrotonate, sodium methoxide, and DBU in the manner previously described to form the corresponding 3-(5-amino-6-methoxy-disubstituted-phenyl)-6-trifluoromethyl-2,4-(1H,3H)-pyrimidinedione (LL). The pyrimidinedione (LL) is in turn reacted with an alkyl halide in the manner described previously to form the corresponding 3-(5-amino-6-methoxy-disubstituted-phenyl)-1-alkyl-6-trifluoromethyl-2,4-(1H,3H)-pyrimidinedione (L-1). The pyrimidinedione (L) is reacted with sodium nitrite and sodium azide under acidic conditions, yielding the corresponding 3-(5-azido-2,4-disubstituted-phenyl)-1-alkyl-6-trifluoromethyl-2,4-(1H,3H)-pyrimidinedione (M). The pyrimidinedione (L-1) is treated with boron tribromide and methylene chloride to form the appropriate 3-(5-amino-6-hydroxy-disubstituted-phenyl)-1-alkyl-6-trifluoromethyl-2,4-(1H,3H)-pyrimidinedione (M-1). The pyrimidinediones (M or M-1) are in turn treated with phosphorous pentoxide and hexamethyidisiloxane and then reacted with either an organic acid, for example acetic, chloroacetic, benzoic, substituted benzoic, or methoxyacetic acid, or with the potassium salt of ethyl malonate, affording the targeted 3-(trisubstituted-benzoxazol-7-yl)-1-alkyl-6-trifluoromethyl-2,4-(1H,3H)-pyrimidinedione (V). The appropriate pyrimidinedione (M-1) can also be treated with cyanogen bromide or reacted with potassium ethyl xanthate in the presence of an alcohol to form the targeted 3-(disubstituted-2-amino- or -2-thiobenzoxazol-7-yl)-1-alkyl-6-trifluoromethyl-2,4-(1H,3H)-pyrimidinedione (V), respectively. The pyrimidinedione (M-1) can also be reacted with 1,1'-carbonyidiimidazole to form the appropriate 3-(disubstituted-2-oxo-2,3-dihydrobenzoxazol-7-yl)-1-alkyl-6-trifluoromethyl-2,4-(1H,3H)-pyrimidinedione (M-2). The so-prepared pyrimidinedione (M-2) is in turn reacted with phosphorus oxychloride under basic conditions, affording the targeted 3-(disubstituted-2-chlorobenzoxazol-7-yl)-1-alkyl-6-trifluoromethyl-2,4-(1H,3H)-pyrimidinedione (VI). The targeted 3-(disubstituted-2-chlorobenzoxazol-7-yl)-1-alkyl-6-trifluoromethyl-2,4-(1H, 3H)-pyrimidinedione (VI) is in turn reacted with an alcohol under basic conditions, affording the targeted 3-(disubstituted-2-alkoxybenzoxazol-7-yl)-1-alkyl-6-trifluoromethyl-2,4-(1H,3H)-pyrimidinedione (VII). Examples 6, 16, 18, 19, 24, and 25 provide the detailed procedures for this route.

Additional moieties may also be added to the benzoxazole ring at this point. For example, bromine moieties are added to 3-(2-methyl-4-chloro-6-fluorobenzoxazol-7-yl)-1-methyl-6-trifluoromethyl-2,4-(1H,3H)-pyrimidinedione by reacting it with N-bromosuccinimide under basic conditions, yielding the corresponding 3-(2-dibromomethyl-4-chloro-6-fluorobenzoxazol-7-yl)-1-methyl-6-trifluoromethyl-2,4-(1H,3H)-pyrimidinedione (VB). An alkyl group can also be added to 3-(2-thio-4-chloro-6-fluorobenzoxazol-7-yl)-1-methyl-6-trifluoromethyl-2,4-(1H,3H)-pyrimidinedione by reacting it with an alkyl halide in the manner described previously, yielding the appropriate 3-(2-alkylthio-4-chloro-6-fluorobenzoxazol-7-yl)-1-methyl-6-trifluoromethyl-2,4-(1H,3H)-pyrimidinedione (VC). In addition, (V), where R in the 2-position is amino may be further reacted to add additional moieties to the amine. For example, an acetyl moiety is added to 3-(2-amino-4-chloro-6-fluorobenzoxazol-7-yl)-1-methyl-6-trifluoromethyl-2,4-(1H,3H)-pyrimidinedione by reacting it with acetyl chloride in the presence of pyridine affording 3-(2-acetylamino-4-chloro-6-fluorobenzoxazol-7-yl)-1-methyl-6-trifluoromethyl-2,4-(1H,3H)-pyrimidinedione (VD). The so-prepared pyrimidinedione (VD) is in turn reacted with sodium hydride and methanesulfonyl chloride to form the appropriate 3-[2-(N-acetyl-N-methylsulfonylamino)-disubstituted-benzoxazol-7-yl]-1-methyl-6-trifluoromethyl-2,4-(1H,3H)-pyrimidinedione (VE), which is hydrogenated under acidic conditions affording 3-(2-methylsulfonylamino-disubstituted-benzoxazol-7-yl)-1-methyl-6-trifluoromethyl-2,4-(1H,3H)-pyrimidinedione (VF). The pyrimidinedione (VF) is in turn alkylated in the manner described previously, affording 3-[2-(N-alkyl-N-methylsulfonyl-amino)-disubstituted-benzoxazol- 7-yl]-1-methyl-6-trifluoromethyl-2,4-(1H,3H)-pyrimidinedione (VG). Examples 14, 17, 20, 21, 22, and 23 provide the detailed procedures for this route.

As depicted in Schema 3, the 3-(substituted-benzothiazol-7-yl)-1-substituted-6-trifluoromethyl-2,4-(1H,3H)-pyrimidinediones are prepared from either of two starting materials, depending upon whether the substituent R in the 2-position of the benzothiazole ring is halogen or alkyl. Those compounds in which the substituent in the 2-position is an alkyl group are prepared by cyclizing a 2,4-, 2,5- or a 2,6-disubstituted-phenylisothiocyanate (STM4) with an alkylmagnesium chloride under basic conditions, yielding the corresponding 2-alkyl-(4- or 6-substituted)benzothiazole (N), for example, 2-methyl-6-fluorobenzothiazole.

Those compounds in which the substituent R in the 2-position of the benzothiazole ring is halogen are prepared by reacting 2-amino-(4- or 6-substituted)benzothiazole (STM5) with t-butyl nitrite and copper(II) chloride to form the corresponding 2-halo-(4- or 6-substituted)benzothiazole (N-1), for example, 2-chloro-6-fluorobenzothiazole. The benzothiazoles (N or N-1) are in turn nitrated with nitric acid and sulfuric acid to form the corresponding 2,4- or 2,6-disubstituted-7-nitrobenzothiazole (O). The so-prepared 7-nitrobenzothiazoles (O) where R in the 2-position of the benzothiazole ring is halogen may then be reacted to replace the 2-halogen with other moieties. For example, 2,4-dichloro-7-nitrobenzothiazole is reacted with piperidine, affording the corresponding 2-(1-piperidinyl)-4- or 6-substituted-7-nitrobenzothiazole (O-1). The 7-nitrobenzothiazoles (O or O-1) are then reduced with iron powder and hydrochloric acid, yielding the corresponding 7-amino-(2,4- or 2,6-disubstituted)benzothiazole (P).

At this point the 7-aminobenzothiazole (P), where R in the 2-position is halogen, alkyl, or other, such as 1-piperidinyl, may be treated directly with ethyl chloroformate to form the corresponding ethyl benzothiazolylcarbamate (Q), or with phosgene to form the corresponding benzothiazolylisocyanate (R-1). In an alternate method, (P), where R in the 2-position is halogen, may be reacted to replace the halogen with other moieties, or to add additional moieties to the benzothiazole ring. For example, (P), where R in the 2-position is chlorine, is reacted with sodium thiomethoxide, yielding the corresponding 7-amino-2-methylthio-(4- or 6-substituted)benzothiazole (P-1); or (P), where R in the 2-position is chlorine, is reacted with N-chlorosuccinimide, yielding the corresponding 7-amino-2,4,6-trichlorobenzothiazole (P-2). The 7-aminobenzothiazoles (P-1) prepared as outlined above may now be reacted with ethyl chloroformate to form the corresponding ethyl benzothiazolylcarbamates (Q), or the 7-aminobenzothiazoles (P-2) may be reacted with phosgene to form the corresponding benzothiazolylisocyanates (R-1). Examples 9 and 10 provided the detailed procedures for these methods.

Additional moieties may also be added to the ethyl benzothiazolylcarbamate (Q) at this point. For example, a chlorine moiety is added to ethyl (2-chloro- or 2-methyl-6-fluorobenzothiazol-7-yl)carbamate by treating it with N,N-dichlorourethane under acidic conditions, yielding the corresponding ethyl (2-substituted-4-chloro-6-fluorobenzothiazol-7-yl)carbamate (Q-1). In addition, (Q-1), where R in the 2-position is chlorine, may be further reacted to substitute other moieties in the 2-position. For example, ethyl (2,4-dichloro-6-fluorobenzothiazol-7-yl)carbamate (Q-1) is reacted with 2-methylpropylamine, affording ethyl (2-methylpropyl-4-chloro-6-fluorobenzothiazol-7-yl)carbamate (Q-2). Examples 11, 12, and 13 provide the detailed procedures for these methods.

By the methods previously described, the ethyl benzothiazolylcarbamates (Q, Q-1, or Q-2) and the benzothiazolylisocyanates (R-1) are then cyclized to the corresponding pyrimidinediones (S) with ethyl 3-amino-4,4,4-trifluorocrotonate in the presence of DBU, which are in turn alkylated, yielding the targeted 3-(2,4- or 2,6- or 2,4,6-substituted-benzothiazol-7-yl)-1-alkyl-6-trifluoromethyl-2,4-(1H,3H)-pyrimidinedione (VIII). In one case alkylation of (S) resulted not only in alkylation at the expected 1-position of the pyrimidinedione ring, but also replaced the chlorine in the 4-position of the benzothiazole ring with methoxy. Examples 7 and 10 provide the detailed procedures for this route.

Once the pyrimidinedione ring (VIII) is formed, additional substituents may be optionally added. For example, a chlorine moiety is added to the 3-(2-chloro-6-fluorobenzothiazol-7-yl)-1-methyl-6-trifluoromethyl-2,4-(1H,3H)-pyrimidinedione molecule by treating it with N-chlorosuccinimide under acidic conditions, affording 3-(2-chloro-6-fluorobenzothiazol-7-yl)-1-methyl- 5-chloro-6-trifluoromethyl-2,4-(1H,3H)-pyrimidinedione (IX). Example 8 provides the detailed procedure for this method.

Schema 1

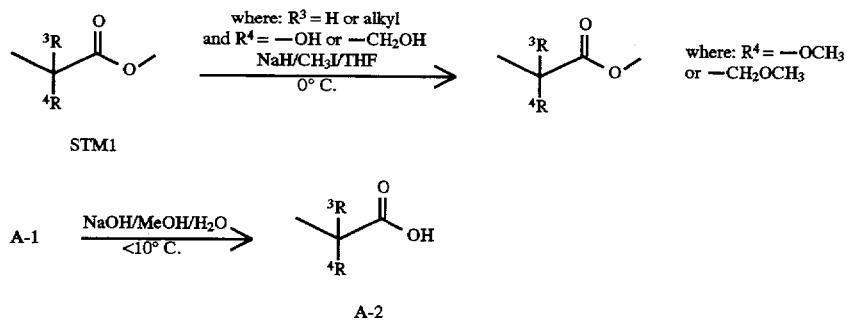

STM1

A-2

-continued
Schema 1
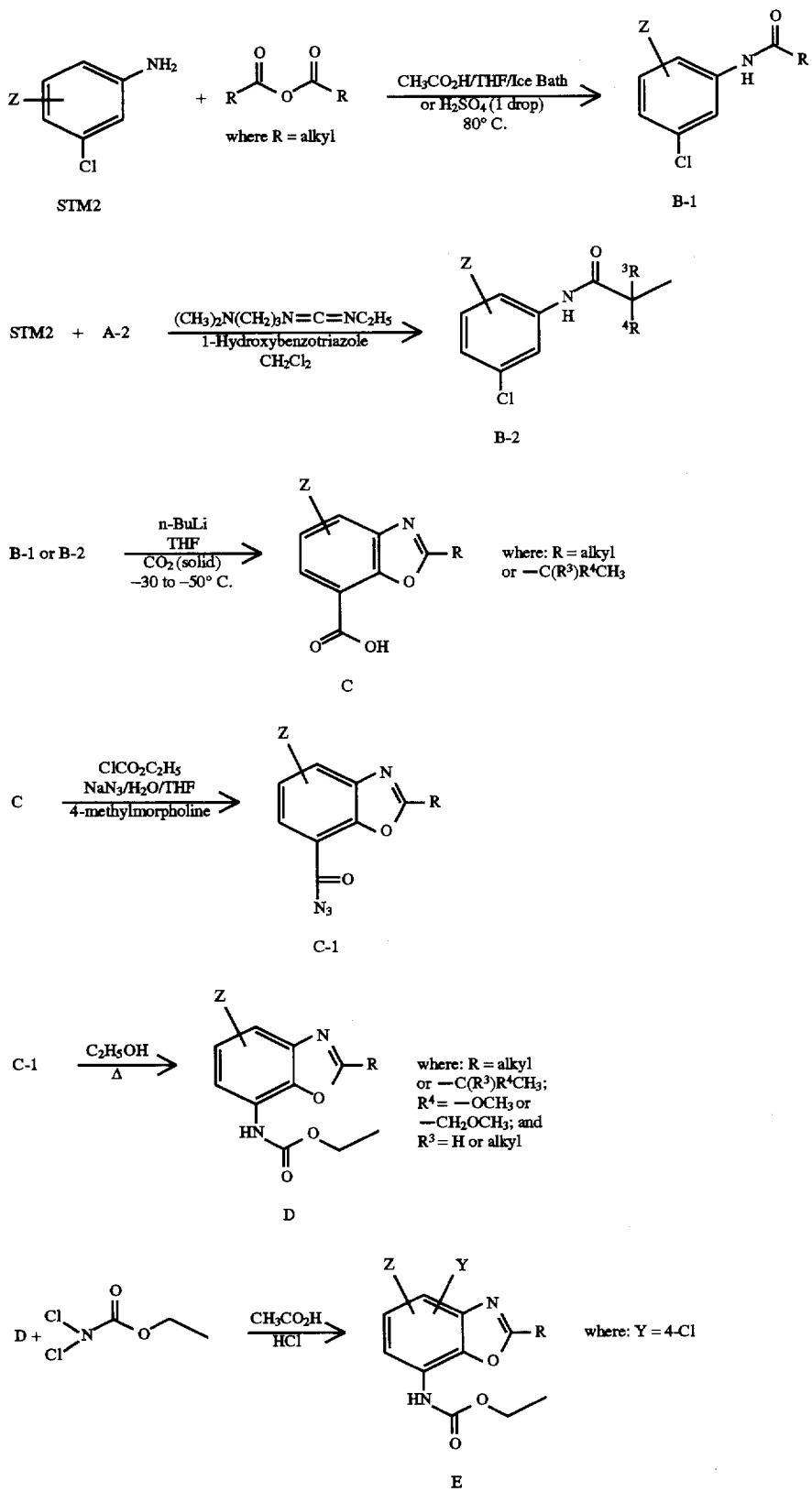

-continued
Schema 1
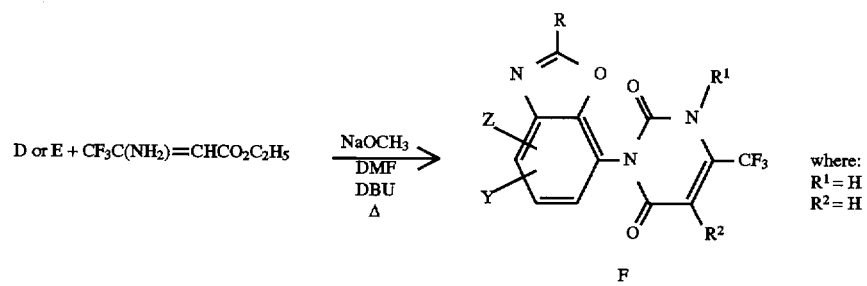
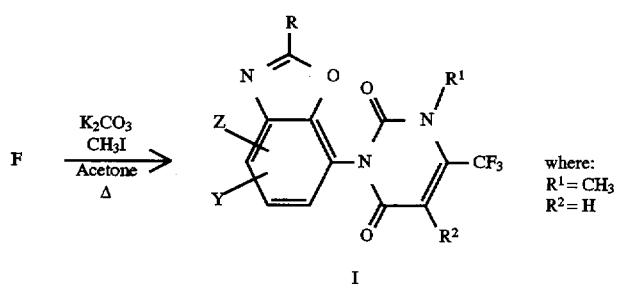
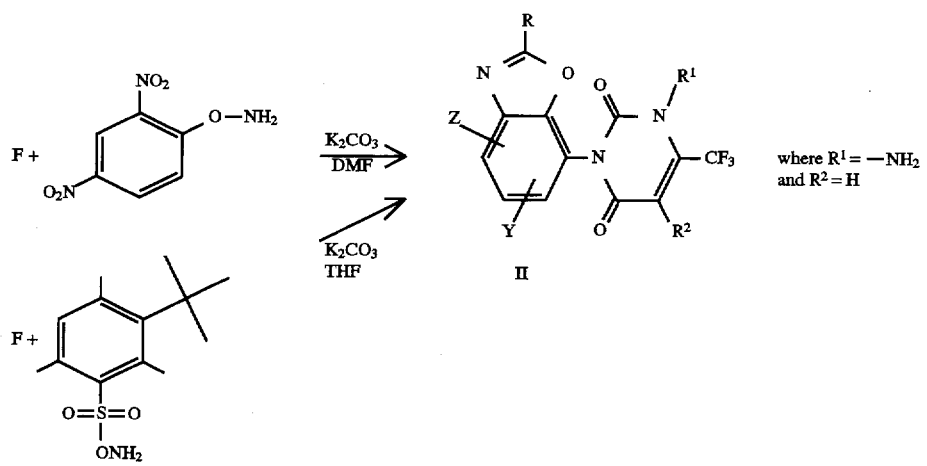
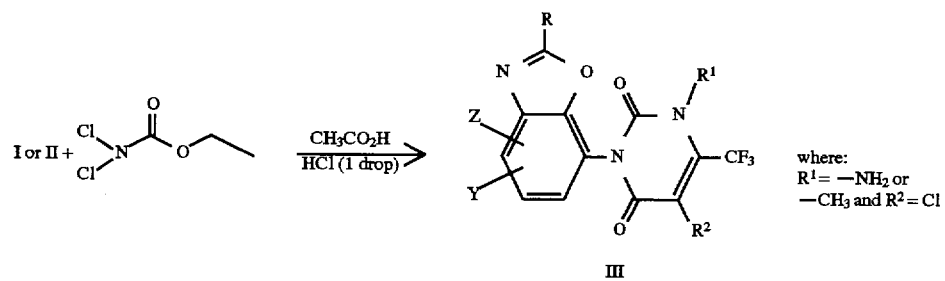

-continued
Schema 1
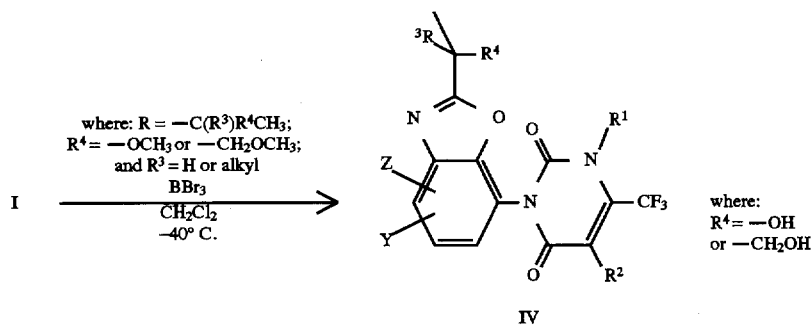
Schema 2
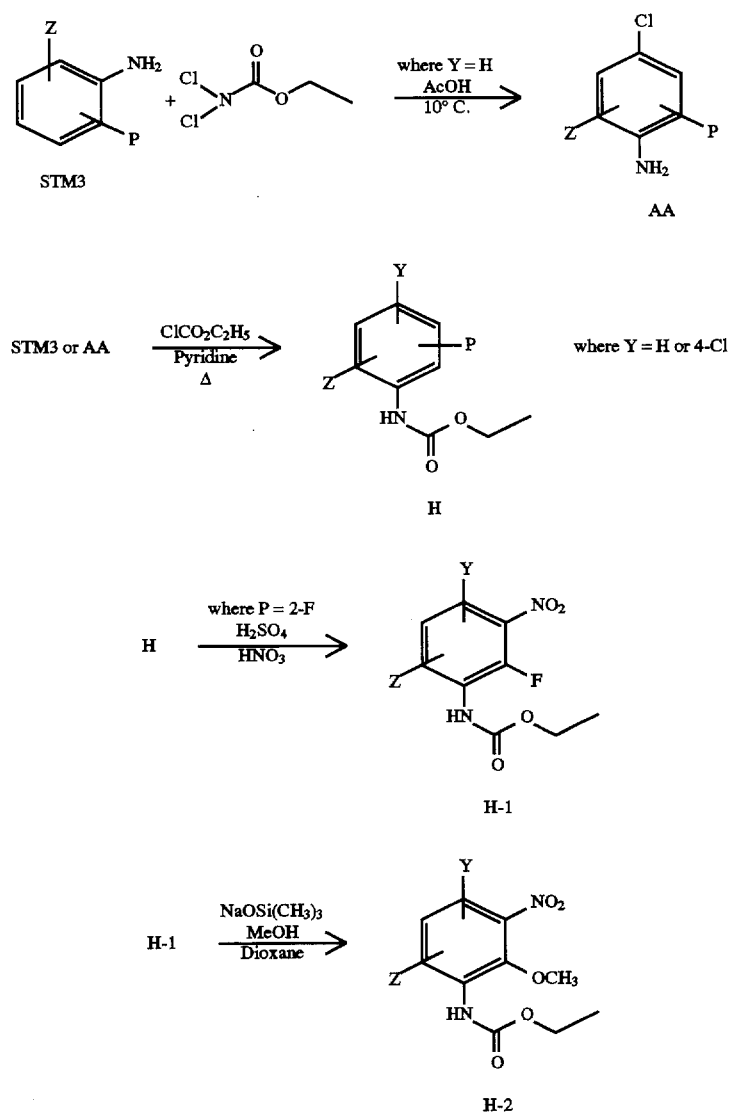

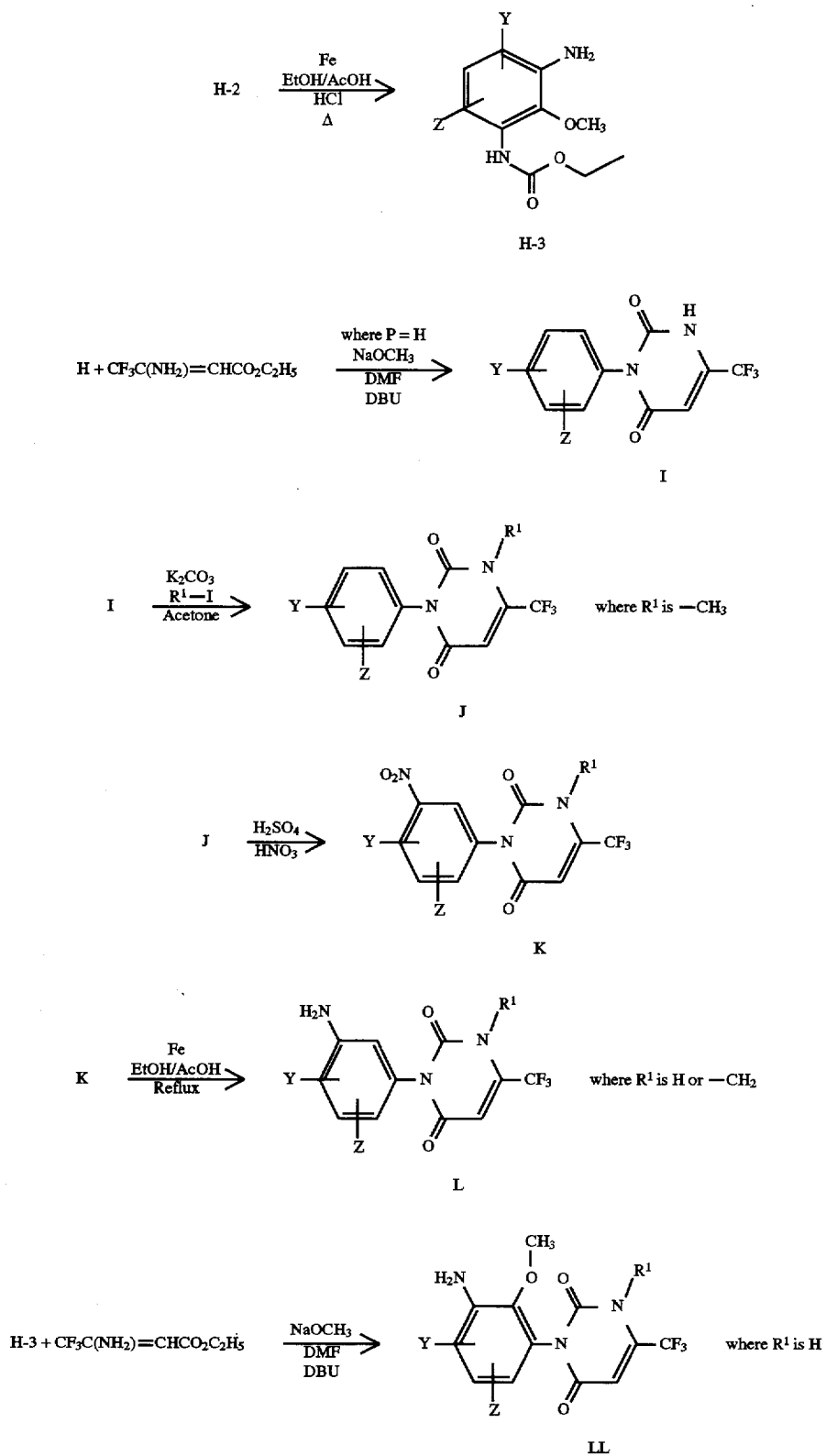

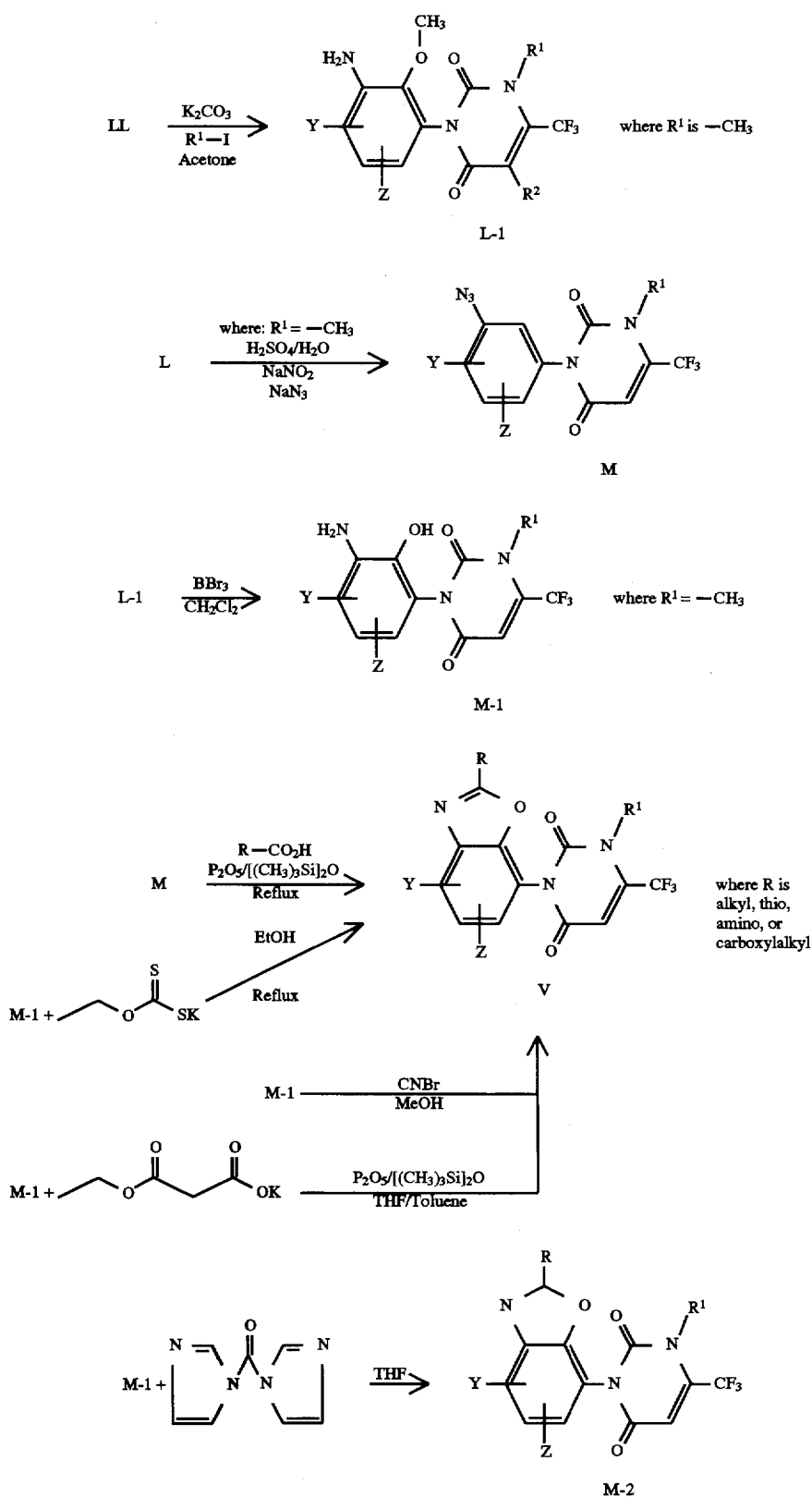

-continued
Schema 2
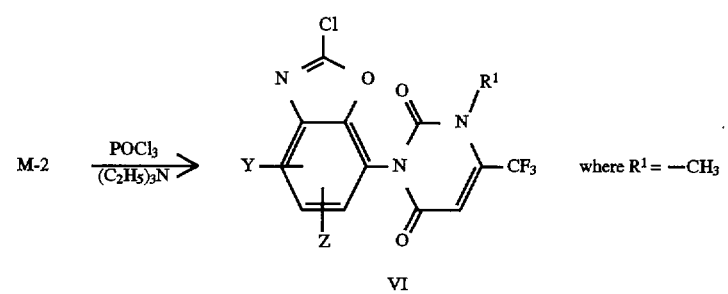
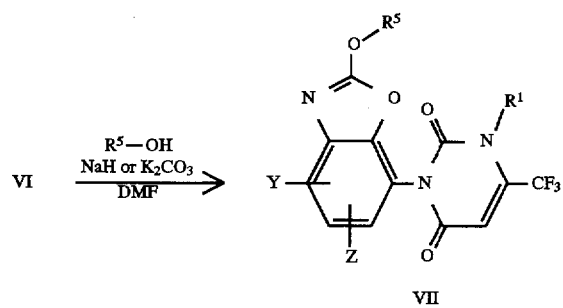
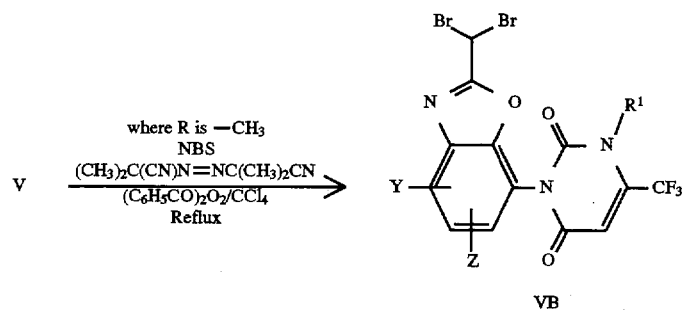
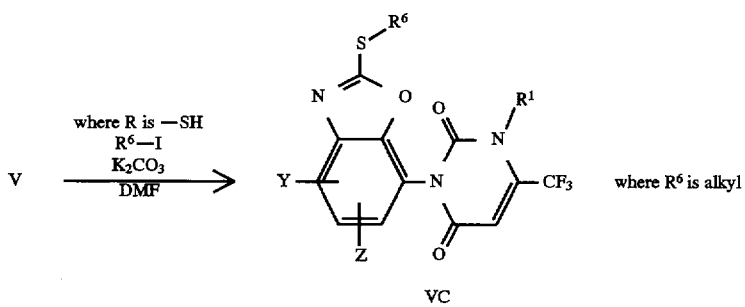
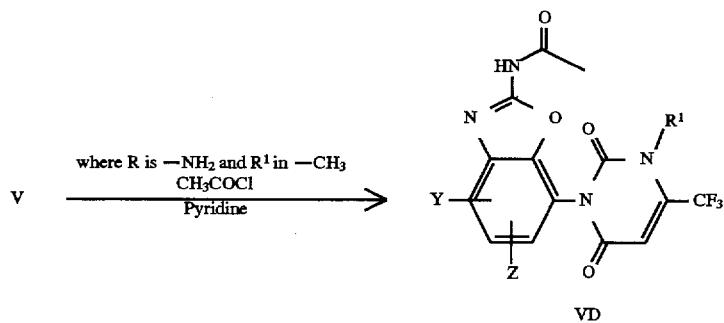

-continued
Schema 2
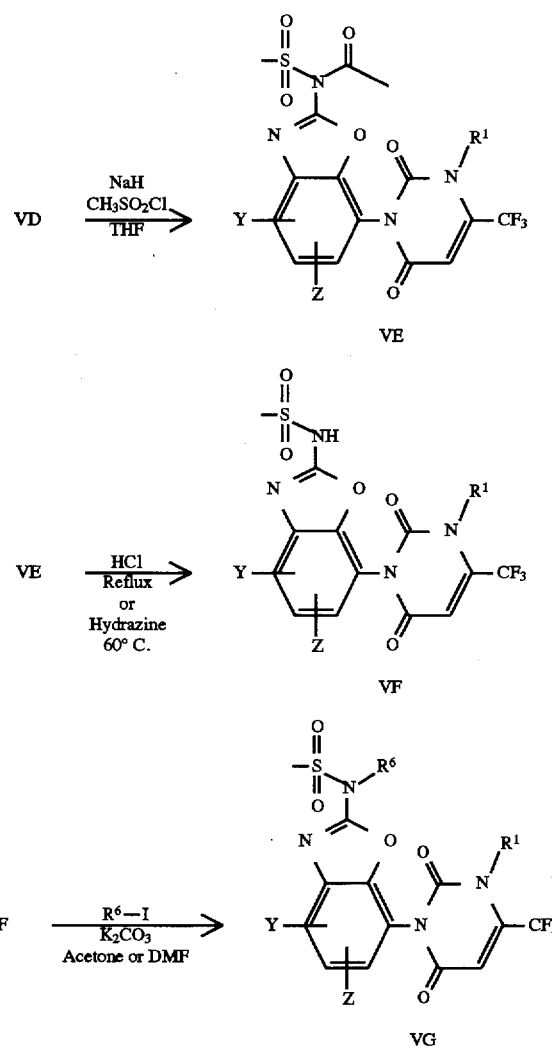
Schema 3
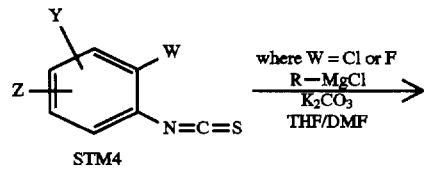
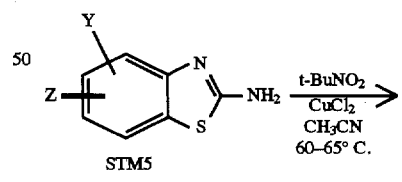
-continued
Schema 3
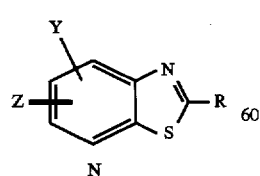
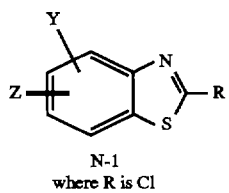

-continued
Scheme 3
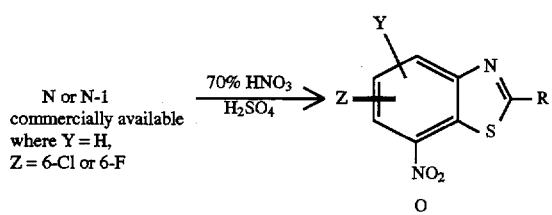
N or N-1 commercially available where Y = H, Z = 6-Cl or 6-F
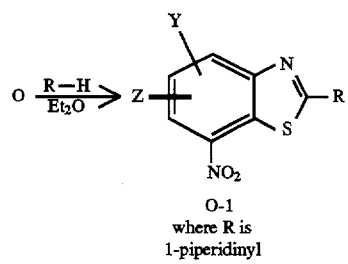
O-1 where R is 1-piperidinyl
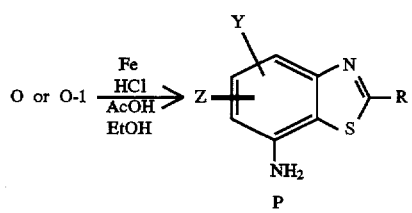
P
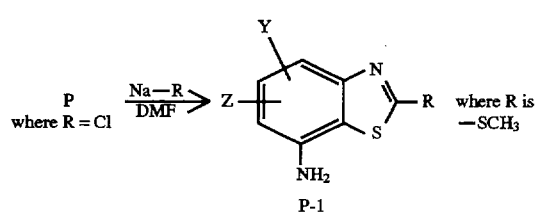
P-1
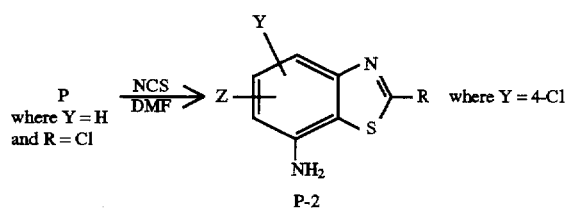
P-2
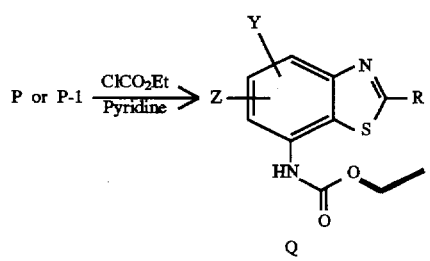
Q
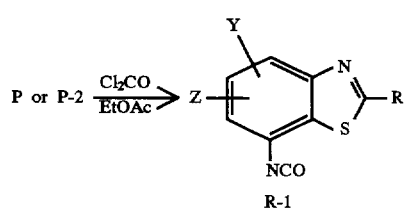
R-1
-continued
Scheme 3
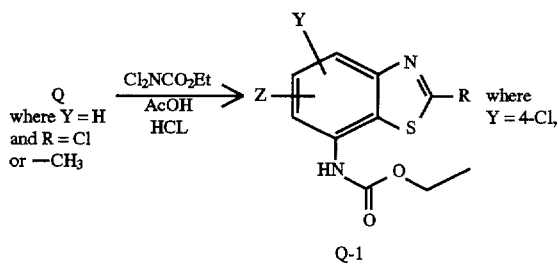
Q-1
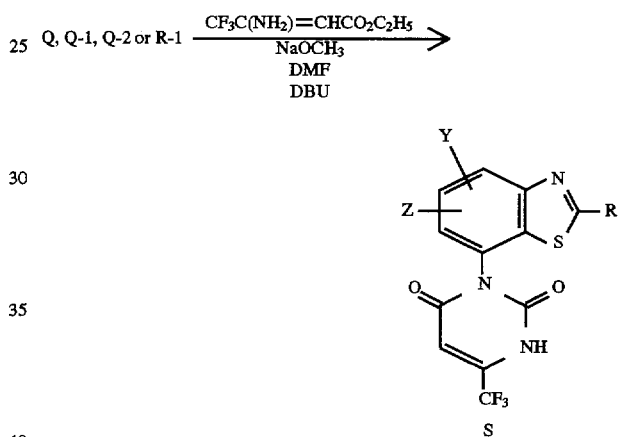
Q-2
Q, Q-1, Q-2 or R-1 $\xrightarrow[\text{NaOCH}_3]{\text{CF}_3\text{C(NH}_2)=\text{CHCO}_2\text{C}_2\text{H}_5}$ DMF DBU
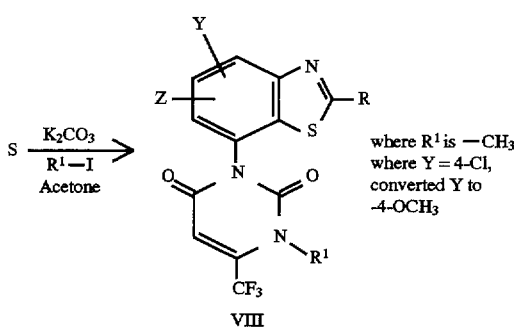
S
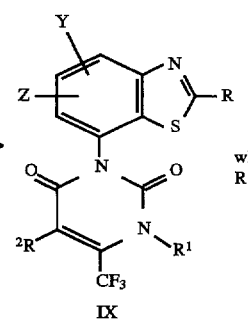
VIII
T where Y = H and R = Cl $\xrightarrow[\text{DMF}]{\text{NCS} \atop \text{AcOH}}$
where Y = 4-Cl, R = Cl, R$^2$ = Cl
IX

EXAMPLE 1

Synthesis of 3-(2-t-butyl-4-chloro-6-fluorobenzoxazol-7-yl)-1-methyl-6-trifluoromethyl-2,4-(1H,3H)pyrimidinedione (Compound 4)

Step A Synthesis of N-(3-chloro-4-fluorophenyl)-t-butylamide as an Intermediate

A solution of 10 grams (69 mmole) of 3-chloro-4-fluoroaniline, 75 mL of acetic acid, and 10 mL of tetrahydrofuran was stirred and cooled in an ice bath. During 15 minutes, 20 mL of trimethylacetic anhydride was added dropwise. Upon completion of the addition the reaction mixture was allowed to warm to ambient temperature, where it stirred for six hours. The reaction mixture was then poured into 300 mL of ice-water and stirred for 15 minutes. The resulting precipitate was collected by filtration and washed with water. The precipitate was purified by column chromatography on silica gel with 4:1 hexane:ethyl acetate as eluant. The product-containing fractions were combined and concentrated under reduced pressure, yielding 10 grams of N-(3-chloro-4-fluorophenyl)-t-butylamide. The NMR spectrum was consistent with the proposed structure.

Step B Synthesis of (2-t-butyl-6-fluorobenzoxazol-7-yl) carboxylic acid as an Intermediate Under a nitrogen atmosphere a stirred solution of 5.0 grams (22 mmole) of N-(3-chloro-4-fluorophenyl)-t-butylamide in 100 mL of tetrahydrofuran was cooled to about −50° C., and 18 mL (45 mmole) of 2.5M n-butyllithium in hexanes was added dropwise at a rate to maintain the reaction mixture temperature below −30° C. Upon completion of the addition the reaction mixture was stirred for 90 minutes and poured over solid carbon dioxide. The mixture was allowed to warm to ambient temperature, and 150 mL of aqueous 1N sodium hydroxide solution was added. The mixture was extracted with two 50 mL portions of ethyl acetate. The organic extracts were combined and washed with 50 mL of aqueous 1N sodium hydroxide solution. The combined washes were acidified to a pH of 2 with concentrated hydrochloric acid and extracted with three 50 mL portions of ethyl acetate. The extracts were combined and washed with aqueous saturated sodium chloride solution. The organic layer was dried with magnesium sulfate and filtered. The filtrate was concentrated under reduced pressure, yielding 3.8 grams of (2-t-butyl-6-fluorobenzoxazol-7-yl)carboxylic acid. The NMR spectrum was consistent with the proposed structure.

Step C Synthesis of ethyl N-(2-t-butyl-6-fluorobenzoxazol-7-yl) carbamate as an Intermediate Under a nitrogen atmosphere a stirred solution of 3.7 grams (15.5 mmole) of (2-t-butyl-6-fluorobenzoxazol-7-yl) carboxylic acid in 40 mL of tetrahydrofuran was cooled in an ice bath, and 1.6 grams (16 mmole) of 4-methylmorpholine was added slowly. To this was then added 1.5 mL (16 mmole) of ethyl chloroformate during a five minute period. Upon completion of the addition the reaction mixture was stirred for 30 minutes, after which a solution of 2.0 grams (32 mmole) of sodium azide in 20 mL of water was added dropwise during a 20 minute period. The reaction mixture was allowed to warm to ambient temperature as it stirred for 30 minutes. The reaction mixture was then analyzed by thin layer chromatography (TLC), which indicated that no starting acid remained. The reaction mixture was poured into 150 mL of aqueous 5% hydrochloric acid solution, and the mixture was extracted with diethyl ether. The combined extract was washed with an aqueous saturated sodium chloride solution, dried with magnesium sulfate, and filtered. The filtrate was concentrated under reduced pressure, yielding 3.4 grams of the azide intermediate as a yellow oil, which was taken up in 50 mL of ethanol and heated at reflux for 18 hours. After this time TLC analysis indicated that the reaction to the carbamate was complete. The reaction mixture was concentrated under reduced pressure, taken up in 50 mL of aqueous 1N hydrochloric acid solution, and extracted with three 50 mL portions of diethyl ether. The combined extracts were washed with an aqueous saturated sodium chloride solution, dried with magnesium sulfate, and filtered. The filtrate was concentrated under reduced pressure, yielding 3.2 grams of ethyl N-(2-t-butyl-6-fluorobenzoxazol-7-yl)carbamate. The NMR spectrum was consistent with the proposed structure.

Step D Synthesis of ethyl N-(2-t-butyl-4-chloro-6-fluorobenzoxazol-7-yl)carbamate as an Intermediate Under a nitrogen atmosphere, a solution of 3.1 grams (11.0 mmole) of ethyl N-(2-t-butyl-6-fluorobenzoxazol-7-yl)carbamate, 35 mL of acetic acid, and 0.2 mL (2.4 mmole) of concentrated hydrochloric acid was stirred and cooled in an ice bath. During five minutes 2.2 grams (14 mmole) of N,N-dichlorourethane was added via syringe. Upon completion of the addition the reaction mixture was stirred for 4 hours, then analyzed by TLC, which indicated the reaction was complete. The reaction mixture was poured into 100 mL of water, and 15 mL of aqueous saturated sodium bicarbonate solution was carefully added. The reaction mixture was then extracted with two 75 mL portions of diethyl ether, and the combined extracts were concentrated under reduced pressure, yielding a residual oil. The oil was subjected to column chromatography on silica gel with 8:1 hexane:ethyl acetate as the eluant. The product-containing fractions were combined and concentrated under reduced pressure, yielding 2.4 grams of ethyl N-(2-t-butyl-4-chloro-6-fluorobenzoxazol-7-yl)carbamate, m.p. 127°−129° C. The NMR spectrum was consistent with the proposed structure.

Step E Synthesis of 3-(2-t-butyl-4-chloro-6-fluorobenzoxazol-7-yl)-6-trifluoromethyl-2,4-(1H,3H) pyrimidinedione as an Intermediate Under a nitrogen atmosphere a solution of 0.33 gram (6.2 mmole) of sodium methoxide in 45 mL of N,N-dimethylformamide was stirred and cooled in an ice bath. During 10 minutes a solution of 1.14 grams (6.2 mmole) of ethyl 3-amino-4,4,4-trifluorocrotonate in 10 mL of N,N-dimethylformamide was added dropwise. Upon completion of the addition the reaction mixture was stirred for 30 minutes, after which a solution of 1.8 grams (5.9 mmole) of ethyl N-(2-t-butyl-4-chloro-6-fluorobenzoxazol-7-yl) carbamate in 30 mL of N,N-dimethylformamide was added dropwise during a 15 minute period. The reaction mixture was heated to 50° C., and 0.91 gram (6 mmole) of 1,8-diazabicyclo[5.4.0]undec-7-ene was added via pipette. Upon completion of the addition the reaction mixture was heated at 120°−125° C. for 24 hours, then cooled to ambient temperature, where it stirred for 24 hours. After this time the reaction mixture was poured into 100 mL of aqueous 10% lithium chloride solution and acidified with concentrated hydrochloric acid. The mixture was then extracted with three 50 mL portions of ethyl acetate. The combined extracts were concentrated under reduced pressure, yielding a black oil, which was extracted with four 50 mL portions of aqueous saturated sodium bicarbonate solution. The combined extracts were acidified with concentrated hydrochloric acid and then extracted with three 40 mL portions of ethyl acetate. The combined extracts were dried with magnesium sulfate and filtered. The filtrate was concentrated under reduced pressure, yielding 0.34 gram of a dark oil. The black oil collected earlier was purified by column chromatography on silica gel. Elution was accomplished with 3:1 hexane-:ethyl acetate. The product-containing fractions were combined and concentrated under reduced pressure, yielding 0.65 gram of a brown solid. The brown solid and the dark oil were combined, yielding 3-(2-t-butyl-4-chloro-6-fluorobenzoxazol-7-yl)-6-trifluoromethyl-2,4-(1H,3H) pyrimidinedione. The NMR spectrum was consistent with the proposed structure.

An alternative method used for preparing the 3-(2-t-butyl-4-chloro-6-fluorobenzoxazol-7-yl)-6-trifluoromethyl-2,4-(1H,3H)pyrimidinedione intermediate is as follows. Under a nitrogen atmosphere a solution of 2.4 grams (45 mmole) of sodium methoxide in 40 mL of N,N-dimethylformamide was stirred and cooled in an ice bath. During 15 minutes a solution of 8.2 grams (45 mmole) of ethyl 3-amino-4,4,4-trifluorocrotonate in 40 mL of N,N-dimethylformamide was added dropwise. Upon completion of the addition the reaction mixture was stirred at 10° C. for 1.5 hours, after which a solution of 13.0 grams (41 mmole) of ethyl N-(2-t-butyl-4-chloro-6-fluorobenzoxazol-7-yl)carbamate (prepared in the manner of Steps A–D, Example 1) in 40 mL of N,N-dimethylformamide was added dropwise during a 15 minute period. Upon completion of the addition the reaction mixture was warmed to ambient temperature, where it stirred for five minutes, then was heated to 60° C., and 6.8 grams (45 mmole) of 1,8-diazabicyclo[5.4.0]undec-7-ene was added via pipette. Upon completion of the addition, the reaction mixture was heated at 120° C. for 4 hours, then cooled to ambient temperature, where it stirred for about 18 hours. The reaction mixture was poured into 200 mL of aqueous 10% potassium carbonate, 100 mL of water was added, and the mixture was extracted with two 100 mL portions of diethyl ether. The combined extracts were washed with 50 mL of aqueous saturated sodium bicarbonate solution. The combined aqueous layer and washes were acidified with about 30 mL of concentrated hydrochloric acid, and the mixture was extracted with three 100 mL portions of ethyl acetate. The combined organic extracts were washed with two 50 mL portions of aqueous saturated sodium chloride solution and two 50 mL portions of aqueous 10% lithium chloride solution. The organic layer was dried with magnesium sulfate, filtered, and concentrated under reduced pressure, yielding 6.4 grams of 3-(2-t-butyl-4-chloro-6-fluorobenzoxazol-7-yl)-6-trifluoromethyl-2,4-(1H,3H) pyrimidinedione, a dark oil. The NMR spectrum was consistent with the proposed structure.

Step F Synthesis of 3-(2-t-butyl-4-chloro-6-fluorobenzoxazol-7-yl)-1-methyl-6-trifluoromethyl-2,4-(1H,3H)pyrimidinedione (Compound 4)

A stirred solution of 0.85 gram (2.1 mmole) of 3-(2-t-butyl-4-chloro-6-fluorobenzoxazol-7-yl)-6-trifluoromethyl-2,4-(1H,3H)pyrimidinedione, 0.48 gram (3.5 mmole) of potassium carbonate, 0.91 gram (6.4 mmole) of iodomethane, and 35 mL of acetone was heated at 40° C. for 2 hours, then stirred at ambient temperature for 20 hours. The reaction mixture was concentrated under reduced pressure, and the concentrate was extracted with two 50 mL portions of diethyl ether. The combined extracts were dried with magnesium sulfate and filtered. The filtrate was concentrated under reduced pressure to a yellow oil, which was subjected to column chromatography on silica gel. Elution was accomplished with 8:1 hexane:ethyl acetate. The product-containing fractions were combined and concentrated under reduce pressure, yielding 0.60 gram of 3-(2-t-butyl-4-chloro-6-fluorobenzoxazol-7-yl)-1-methyl-6-trifluoromethyl-2,4-(1H,3H)pyrimidinedione, m.p. 68°–70° C. The NMR spectrum was consistent with the proposed structure.

An alternative method for preparing 3-(2-t-butyl-4-chloro-6-fluorobenzoxazol-7-yl)-1-methyl-6-trifluoromethyl-2,4-(1H,3H)pyrimidinedione is the following: A solution of 16.0 grams (39 mmole) of 3-(2-t-butyl-4-chloro-6-fluorobenzoxazol-7-yl)-6-trifluoromethyl-2,4-(1H,3H) pyrimidinedione, 8.3 grams (60 mmole) of potassium carbonate, 8.5 grams (60 mmole) of iodomethane, and 150 mL of acetone was stirred at ambient temperature for about 18 hours. The reaction mixture was then concentrated under reduced pressure, and the residue was taken up in aqueous 5% hydrochloric acid. The mixture was extracted with three 75 mL portions of diethyl ether. The combined extracts were washed with aqueous saturated sodium chloride solution. The organic layer was dried with magnesium sulfate, filtered, and concentrated under reduced pressure, yielding 12.7 grams of a dark oil, which was subjected to column chromatography on silica gel. Elution was accomplished with 6:1 heptane:ethyl acetate. The product-containing fractions were combined and concentrated under reduced pressure, yielding 9.4 grams of 3-(2-t-butyl-4-chloro-6-fluorobenzoxazol-7-yl)-1-methyl-6-trifluoromethyl-2,4-(1H,3H)pyrimidinedione. The NMR spectrum was consistent with the proposed structure.

EXAMPLE 2

Synthesis of 3-(2-t-butyl-4-chlorobenzoxazol-7-yl)-1-methyl-6-trifluoromethyl-2,4-(1H,3H) pyrimidinedione (Compound 1)

Step A Synthesis of N-(2,5-dichlorophenyl)-t-butylamide as an Intermediate

Under a nitrogen atmosphere a stirred solution of 5.0 grams (31 mmole) of 2,5-dichlorcaniline, 6.5 grams (35 mmole) of trimethylacetic anhydride, and 1 drop of concentrated sulfuric acid was heated at about 80° C. for four hours, after which analysis by thin layer chromatography (TLC) indicated that the reaction was complete. The reaction mixture was poured into 150 mL of aqueous 1N hydrochloric acid and stirred for 30 minutes. The resulting precipitate was collected by filtration and washed with water. The filtrate and washes were combined and dried in a vacuum oven at 45° C. for about 16 hours, yielding 7.3 grams of N-(2,5-dichlorophenyl)-t-butylamide. The NMR spectrum was consistent with the proposed structure.

Step B Synthesis of (2-t-butyl-4-chlorobenzoxazol-7-yl) carboxylic acid as an Intermediate This compound was prepared in the manner of Step B, Example 1, with 6.0 grams (24 mmole) of N-(2,5-dichlorophenyl)-t-butylamide, 100 mL of tetrahydrofuran, and 24 mL (60 mmole) of 2.5M n-butyllithium in hexanes as reagents. The yield of (2-t-butyl-4-chlorobenzoxazol-7-yl) carboxylic acid was 4.2 grams. The NMR spectrum was consistent with the proposed structure.

Step C Synthesis of ethyl N-(2-t-butyl-4-chlorobenzoxazol-7-yl)carbamate as an Intermediate This compound was prepared in the manner of Step C, Example 1, with 3.0 grams (11.8 mmole) of (2-t-butyl-4-chlorobenzoxazol-7-yl)carboxylic acid, 40 mL of tetrahydrofuran, 1.21 grams (12 mmole) of 4-methylmorpholine, and 1.3 grams (12 mmole) of ethyl chloroformate as reagents. The yield of ethyl N-(2-t-butyl-4-chlorobenzoxazol-7-yl)carbamate was 2.9 grams. The NMR spectrum was consistent with the proposed structure.

Step D Synthesis of 3-(2-t-butyl-4-chlorobenzoxazol-7-yl)-6-trifluoromethyl-2,4-(1H,3H)pyrimidinedione as an Intermediate This compound was prepared in the manner of Step E, Example 1, with 0.65 gram (12.0 mmole) of sodium methoxide, 45 mL of N,N-dimethylformamide, 2.0 grams (11.0 mmole) of ethyl 3-amino-4,4,4-trifluorocrotonate, 2.9 grams (9.8 mmole) of ethyl N-(2-t-butyl-4-chlorobenzoxazol-7-yl)carbamate, and 1.7 grams (11 mmole) of 1,8-diazabicyclo[5.4.0]undec-7-ene as reagents. The yield of 3-(2-t-butyl-4-chlorobenzoxazol-7-yl)-6-trifluoromethyl-2,4-(1H,3H)pyrimidinedione was 2.8 grams. The NMR spectrum was consistent with the proposed structure.

Step E Synthesis of 3-(2-t-butyl-4-chlorobenzoxazol-7-yl)-1-methyl-6-trifluoromethyl-2,4-(1H,3H)pyrimidinedione (compound 1)

This compound was prepared in the manner of Step F, Example 1, with 2.0 grams (5.2 mmole) of 3-(2-t-butyl-4-chlorobenzoxazol-7-yl)-6-trifluoromethyl-2,4-(1H,3H) pyrimidinedione, 1.1 grams (7.8 mmole) of potassium carbonate, 1.1 grams (8 mmole) of iodomethane, and 50 mL of acetone as reagents. The yield of 3-(2-t-butyl-4-chlorobenzoxazol-7-yl)-1-methyl-6-trifluoromethyl-2,4-(1H,3H)pyrimidinedione, m.p. 146°–148° C., was 1.5 grams. The NMR spectrum was consistent with the proposed structure.

EXAMPLE 3

Synthesis of 3-(2-t-butyl-4-chlorobenzoxazol-7-yl)-1-methyl-5-chloro-6-trifluoromethyl-2,4-(1H,3H)pyrimidinedione (Compound 2)

A stirred solution of 0.84 gram (2.1 mmole) of 3-(2-t-butyl-4-chlorobenzoxazol-7-yl)-1-methyl-6-trifluoromethyl-2,4-(1H,3H)pyrimidinedione (prepared as described in Example 2) in 20 mL of acetic acid had 0.16 gram (1.0 mmole) of N,N-dichlorourethane added via syringe. Upon completion of the addition the clear reaction mixture was stirred for 15 minutes, then one drop of concentrated hydrochloric acid was added, and the reaction mixture was stirred at ambient temperature for 72 hours. After this time the reaction mixture was poured into 100 mL of water, and 10 grams of sodium carbonate were added. The mixture was extracted with three 50 mL portions of methylene chloride. The organic extracts were combined and washed with one 50 mL portion of an aqueous 5% sodium carbonate solution. The organic layer was dried with sodium sulfate and filtered. The filtrate was concentrate under reduced pressure, yielding a pale yellow oil which was subjected to column chromatography on silica gel. Elution was accomplished with 9:1 heptane:ethyl acetate, followed by 2:1 heptane:ethyl acetate. The product-containing fractions were combined and concentrated under reduced pressure, yielding 0.57 gram of 3-(2-t-butyl-4-chlorobenzoxazol-7-yl)-1-methyl-5-chloro-6-trifluoromethyl-2,4-(1H,3H)pyrimidinedione, m.p. 83°–86° C. The NMR spectrum was consistent with the proposed structure.

EXAMPLE 4

Synthesis of 3-(2-t-butyl-4-chlorobenzoxazol-7-yl)-1-amino-6-trifluoromethyl-2,4-(1H,3H)-pyrimidinedione (Compound 3)

A stirred solution of 0.5 gram (1.3 mmole) of 3-(2-t-butyl-4-chlorobenzoxazol-7-yl)-6-trifluoromethyl-2,4-(1H,3H) pyrimidinedione (prepared in Step D, Example 2), 0.21 gram (1.5 mmole) of potassium carbonate, and 30 mL of N,N-dimethylformamide was heated at 60° C. for 20 minutes, cooled to ambient temperature, and 0.30 gram (1.5 mmole) of O-(2,4-dinitrophenyl)-hydroxylamine was added. Upon completion of the addition the reaction mixture was stirred for about 18 hours, then poured into 100 mL of water and extracted with three 40 mL portions of methylene chloride. The combined organic extracts were dried with magnesium sulfate, filtered, and concentrated under reduced pressure, yielding 0.3 gram of a yellow oil. The aqueous layer was neutralized with excess ammonium chloride and extracted with two 50 mL portions of ethyl acetate. The combined extracts were washed with an aqueous saturated sodium chloride solution. The organic layer was dried with magnesium sulfate, filtered, and concentrated under reduced pressure, yielding 0.22 gram of a solid. Thin layer chromatography (TLC) indicated that this solid was the starting material, 3-(2-t-butyl-4-chlorobenzoxazol-7-yl)-6-trifluoromethyl-2,4-(1H,3H)pyrimidinedione. The yellow oil was subjected to column chromatography on silica gel. Elution was accomplished with 5:1 heptane:ethyl acetate. The product-containing fractions were combined and concentrated under reduced pressure, yielding 0.12 gram of 3-(2-t-butyl-4-chlorobenzoxazol-7-yl)-1-amino-6-trifluoromethyl- 2,4-(1H,3H)pyrimidinedione, m.p. 104°–106° C. A solution containing the recovered 3-(2-t-butyl-4-chlorobenzoxazol-7-yl)-6-trifluoromethyl-2,4-(1H,3H)pyrimidinedione, 1.1 grams of potassium carbonate, 10 mL of N,N-dimethylformamide, and 1.1 grams of O-(2,4-dinitrophenyl)hydroxylamine was stirred for about 60 hours. After this time the work-up procedure described above was repeated, yielding 0.7 gram of solid. Analysis by TLC indicated that the solid was 3-(2-t-butyl-4-chlorobenzoxazol-7-yl)-1-amino-6-trifluoromethyl-2,4-(1H,3H)pyrimidinedione, m.p. 104°–106° C. The two materials were combined for a yield of 0.8 gram of 3-(2-t-butyl-4-chlorobenzoxazol-7-yl)-1-amino-6-trifluoromethyl-2,4-(1H,3H)-pyrimidinedione. The NMR spectrum was consistent with the proposed structure.

EXAMPLE 5

Synthesis of 3-(2-t-butyl-4-chloro-6-fluorobenzoxazol-7-yl)-1-amino-6-trifluoromethyl-2,4-(1H,3H)pyrimidinedione (Compound 5)

Step A Synthesis of 1-aminooxysulfonyl-2,4,6-trimethylbenzene as an Intermediate To a stirred solution of 25.0 grams (114 mmole) of 2,4,6-trimethyl-benzenesulfonyl chloride, 15.2 grams (114 mmole) of t-butyl-N-hydroxy-carbamate, and 350 mL of diethyl ether, cooled in an ice bath, was added dropwise 11.4 grams (114 mmole) of triethylamine. Upon completion of the addition the reaction mixture was stirred at ambient temperature for about 18 hours, then filtered, and the filtrate was concentrated under reduced pressure. The concentrate was taken up in toluene and petroleum ether, filtered, and 150 mL of trifluoroacetic acid was added. The reaction mixture was stirred for 1.5 hours in an ice bath, then poured into ice-water, filtered, and extracted with diethyl ether. The organic extract was dried with magnesium sulfate and filtered. Petroleum ether was added to the filtrate, and the resulting precipitate was collected by filtration, yielding 14.4 grams of 1-aminooxysulfonyl-2,4,6-trimethylbenzene. The NMR spectrum was consistent with the proposed structure.

Step B Synthesis of 3-(2-t-butyl-4-chloro-6-fluorobenzoxazol-7-yl)-1-amino-6-trifluoromethyl-2,4-(1H,3H)pyrimidinedione (Compound 5)

Under a nitrogen atmosphere a stirred solution of 1.0 gram (2.5 mmole) of 3-(2-t-butyl-4-chloro-6-fluorobenzoxazol-7-yl)-6-trifluoromethyl-2,4-(1H,3H)

pyrimidinedione (prepared in Example 1, Steps A–E), 0.41 gram (3.0 mmole) of potassium carbonate, and 50 mL of tetrahydrofuran was cooled in an ice bath. To this was added 1.1 grams (about 5 mmole) of 1-aminooxysulfonyl-2,4,6-trimethylbenzene. Upon completion of the addition the reaction mixture was stirred in the ice bath for ten minutes, then warmed to ambient temperature, where it stirred for an additional 18 hours. After this time the reaction mixture was poured into 150 mL of aqueous 10% ammonium chloride solution and extracted with two 75 mL portions of diethyl ether. The combined extracts were washed with two 50 mL portions of an aqueous saturated sodium chloride solution. The organic layer was dried with magnesium sulfate and filtered. The filtrate was concentrated under reduced pressure to an oil, which was subjected to column chromatography on silica gel. Elution was accomplished with 6:1 heptane:ethyl acetate. The product-containing fractions were combined and concentrated under reduced pressure, yielding 0.75 gram of 3-(2-t-butyl-4-chloro-6-fluorobenzoxazol-7-yl)-1-amino-6-trifluoromethyl-2,4-(1H,3H) pyrimidinedione, m.p. 90°–92° C. The NMR spectrum was consistent with the proposed structure.

EXAMPLE 6

Synthesis of 3-(2-methyl-4-chloro-6-fluorobenzoxazol-7-yl)-1-methyl-6-trifluoromethyl-2,4-(1H,3H)pyrimidinedione (Compound 6)

Step A Synthesis of ethyl N-(4-chloro-2-fluorophenyl) carbamate as an Intermediate A solution of 6.9 grams (47 mmole) of 4-chloro-2-fluoroaniline in 75 mL of pyridine was stirred and cooled in an ice bath. During 15 minutes, 5.4 grams (50 mmole) of ethyl chloroformate was added dropwise. Upon completion of the addition the reaction mixture was heated at 60°–70° C. for 1.5 hours, then concentrated under reduced pressure to a residue. The residue was stirred with 150 mL of aqueous 3N hydrochloric acid, and the resulting precipitate was collected by filtration. The precipitate was washed with aqueous 3N hydrochloric acid and then with water. The precipitate was dried under ambient conditions for about 18 hours, then dried under vacuum for two hours, yielding 9.6 grams of ethyl N-(4-chloro-2-fluoro-phenyl)carbamate. The NMR spectrum was consistent with the proposed structure.

Step B Synthesis of 3-(4-chloro-2-fluorophenyl)-6-trifluoromethyl-2,4-(1H,3H)pyrimidinedione as an Intermediate This compound was prepared in a manner analogous to Step E, Example 1 with 1.1 grams (20 mmole) of sodium methoxide, 45 mL of N,N-dimethylformamide, 3.7 grams (20 mmole) of ethyl 3-amino-4,4,4-trifluorocrotonate, 3.8 grams (17.5 mmole) of ethyl N-(4-chloro-2-fluorophenyl) carbamate, and 3.0 grams (20 mmole) of 1,8-diazabicyclo [5.4.0]undec-7-ene as reagents. This reaction differed in that the reaction mixture was heated at 105° C. for four hours rather than 120°–125° C. for 24 hours. The yield of 3-(4-chloro-2-fluorophenyl)-6-trifluoromethyl-2,4-(1H,3H) pyrimidinedione was 4.0 grams. The NMR spectrum was consistent with the proposed structure.

Step C Synthesis of 3-(4-chloro-2-fluorophenyl)-1-methyl-6-trifluoromethyl-2,4-(1H,3H)pyrimidinedione as an Intermediate This compound was prepared in the manner of Step F, Example 1 with 4.0 grams (13.2 mmole) of 3-(4-chloro-2-fluorophenyl)-6-trifluoromethyl-2,4-(1H,3H) pyrimidinedione, 4.2 grams (30 mmole) of potassium carbonate, 4.3 grams (30 mmole) of iodomethane, and 55 mL of acetone as reagents. The yield of 3-(4-chloro-2-fluorophenyl)-1-methyl-6-trifluoromethyl-2,4-(1H,3H)-pyrimidinedione was 3.0 grams. The NMR spectrum was consistent with the proposed structure.

Step D Synthesis of 3-(4-chloro-2-fluoro-5-nitrophenyl)-1-methyl-6-trifluoromethyl-2,4-(1H,3H)pyrimidinedione as an Intermediate A solution of 3.0 grams (9.4 mmole) of 3-(4-chloro-2-fluorophenyl)-1-methyl-6-trifluoromethyl-2,4-(1H,3H) pyrimidinedione in 30 mL of concentrated sulfuric acid was stirred and cooled in an ice bath. During 15 minutes, 0.75 mL (12 mmole) of aqueous 70% nitric acid was added dropwise, after which the reaction mixture was allowed to warm to ambient temperature, where it stirred for two hours. The reaction mixture was then poured into 150 mL of ice-water. The resulting precipitate was collected by filtration, washed with water, and dried under reduced pressure, yielding 3.0 grams of 3-(4-chloro-2-fluoro-5-nitrophenyl)-1-methyl-6-trifluoromethyl-2,4-(1H,3 H)-pyrimidinedione. The NMR spectrum was consistent with the proposed structure.

Step E Synthesis of 3-(5-amino-4-chloro-2-fluorophenyl)-1-methyl-6-trifluoromethyl-2,4-(1H,3H)pyrimidinedione as an Intermediate Under a nitrogen atmosphere a solution of 3.0 grams (8.2 mmole) of 3-(4-chloro-2-fluoro-5-nitrophenyl)-1-methyl-6-trifluoromethyl-2,4-(1H,3H)-pyrimidinedione, and 20 mL of acetic acid in 80 mL of ethanol was stirred, and 1.8 grams (32 mmole) of iron powder was added. The reaction mixture was then heated under reflux for one hour, after which analysis by thin layer chromatography (TLC) indicated that the reaction was complete. The reaction mixture was concentrated under reduced pressure. The concentrate was then taken up in 50 mL of aqueous 5% sodium bicarbonate solution and 100 mL of ethyl acetate. The mixture was filtered through diatomaceous earth, and the filter cake was washed with 20 mL of water and three 50 mL portions of ethyl acetate. The filtrate was placed in a separatory funnel and 100 mL of aqueous 5% sodium bicarbonate solution was added. The aqueous phase was separated and the organic phase was washed with 50 mL of aqueous saturated sodium bicarbonate solution, then with 50 mL of aqueous saturated sodium chloride solution. The organic layer was dried with magnesium sulfate and filtered. The filtrate was concentrated under reduced pressure, yielding 2.6 grams of 3-(5-amino-4-chloro-2-fluorophenyl)-1-methyl-6-trifluoromethyl-2,4-(1H,3H)pyrimidinedione. The NMR spectrum was consistent with the proposed structure.

Step F Synthesis of 3-(5-azido-4-chloro-2-fluorophenyl)-1-methyl-6-trifluoromethyl-2,4-(1H,3H)pyrimidinedione as an Intermediate A stirred solution of 6.0 mL of concentrated sulfuric acid and 15 mL of water was cooled to 5° C. in an ice bath. To this was added 1.6 grams (4.7 mmole) of 3-(5-amino-4-chloro-2-fluorophenyl)-1-methyl-6-trifluoromethyl-2,4-(1H,3H)pyrimidinedione. Over a period of 10 minutes a solution of 0.36 gram (5.2 mmole) of sodium nitrite in 5.0 mL of water was added dropwise at a rate to maintain the reaction mixture temperature below 10° C. Upon completion of the addition the reaction mixture was stirred for 40 minutes at about 5° to 10° C. A solution of 0.37 gram (5.6 mmole) of sodium azide in 5.0 mL of water was then added during a 20 minute period at a rate to maintain the reaction mixture temperature below 10° C. The reaction mixture was then stirred for 20 minutes and poured into 150 mL of water. The resulting precipitate was filtered, washed with water, and dried at ambient conditions for about 18 hours, then at 65° C. for 6 hours under vacuum. The yield of 3-(5-azido-4-chloro-2-fluorophenyl)-1-methyl-6-trifluoromethyl-2,4-(1H,3H)pyrimidinedione was about 1.8 grams. The NMR spectrum was consistent with the proposed structure.

Step G Synthesis of 3-(2-methyl-4-chloro-6-fluorobenzoxazol-7-yl)-1-methyl-6-trifluoromethyl-2,4-(1H,3H)pyrimidinedione (Compound 6)

Under a nitrogen atmosphere a stirred solution of 4.0 grams (28 mmole) of phosphorus pentoxide and 10 mL (47 mmole) of hexamethyldisiloxane was heated at 90° C. for 30 minutes. To this was added dropwise during a 5.0 minute period a solution of 0.80 gram (2.2 mmole) of 3-(5-azido-4-chloro-2-fluorophenyl)-1-methyl-6-trifluoromethyl-2,4-(1H,3H)pyrimidinedione in 5.0 mL of acetic acid. Upon completion of the addition the reaction mixture was heated at reflux for 5.0 hours, cooled to ambient temperature, and poured into 50 mL of water. The reaction mixture was extracted with three 25 mL portions of ethyl acetate. The combined extracts were washed with 50 mL of aqueous saturated sodium bicarbonate solution and 50 mL of aqueous saturated sodium chloride solution. The organic layer was dried with magnesium sulfate and filtered. The filtrate was concentrated under reduced pressure, yielding 0.7 gram of a residual oil, which was subjected to column chromatography on silica gel. Elution was accomplished with 3:1 heptane::ethyl acetate. The product-containing fractions were combined and concentrated under reduced pressure, yielding 0.40 gram of an oily white solid, 3-(2-methyl-4-chloro-6-fluorobenzoxazol-7-yl)-1-methyl-6-trifluoromethyl-2,4-(1H,3H)pyrimidinedione, m.p. 64°–66° C. The NMR spectrum was consistent with the proposed structure.

EXAMPLE 7

Synthesis of 3-(2-chloro-6-fluorobenzothiazol-7-yl)-1-methyl-6-trifluoromethyl-2,4-(1H,3H) pyrimidinedione (Compound 10)

Step A Synthesis of 2-chloro-6-fluoro-7-nitrobenzothiazole as an Intermediate

This compound was prepared in the manner of Step D, Example 6, with 5.0 grams (26.6 mmole) of 2-chloro-6-fluorobenzothiazole, 20 mL of concentrated sulfuric acid, and 2.0 mL (35 mmole) of concentrated nitric acid as reagents. This procedure differed in that the reaction mixture was neutralized with 20 mL of concentrated ammonium hydroxide before the precipitate was filtered. The yield of 2-chloro-6-fluoro-7-nitrobenzothiazole was 4.4 grams. The NMR spectrum was consistent with the proposed structure.

Step B Synthesis of 7-amino-2-chloro-6-fluorobenzothiazole as an Intermediate

This compound was prepared in the manner of Step E, Example 6, with 4.2 grams (18 mmole) of 2-chloro-6-fluoro-7-nitrobenzothiazole, 4.0 grams (72 mmole) of iron powder, 10 mL of acetic acid, 100 mL of ethanol, and 2 mL (24 mmole) of concentrated hydrochloric acid as reagents. The yield of 7-amino-2-chloro-6-fluorobenzothiazole was 2.7 grams. The NMR spectrum was consistent with the proposed structure.

Step C Synthesis of ethyl N-(2-chloro-6-fluorobenzothiazol-7-yl) carbamate as an Intermediate Under a nitrogen atmosphere 20 mL of pyridine was stirred, and 2.7 grams (25 mmole) of ethyl chloroformate was added via syringe. Upon completion of the addition the reaction mixture was stirred for 15 minutes. To this was then added a solution of 2.6 grams (12.8 mmole) of 7-amino-2-chloro-6-fluorobenzothiazole in 30 mL pyridine dropwise during a 15 minute period. The reaction mixture was warmed to ambient temperature, where it stirred for one hour, after which the reaction mixture was poured into 200 mL of 1N aqueous hydrochloric acid. The resulting precipitate was collected by filtration, washed with water, and dried under reduced pressure. The yield of ethyl N-(2-chloro-6-fluorobenzothiazol-7-yl)carbamate was 2.8 grams. The NMR spectrum was consistent with the proposed structure.

Step D Synthesis of 3-(2-chloro-6-fluorobenzothiazol-7-yl)-6-trifluoromethyl-2,4-(1H,3H)pyrimidinedione as an Intermediate This compound was prepared in the manner of Step E, Example 1, with 2.8 grams (10 mmole) of ethyl N-(2-chloro-6-fluorobenzothiazol-7-yl)carbamate, 2.2 grams (12 mmole) of ethyl 3-amino-4,4,4-trifluorocrotonate, 0.6 gram (11 mmole) of sodium methoxide, 30 mL of N,N-dimethylformamide, and 1 mL (7.3 mmole) of 1,8-diazabicyclo[5.4.0]undec-7-ene as reagents. The yield of 3-(2-chloro-6-fluorobenzothiazol-7-yl)-6-trifluoromethyl-2,4-(1H,3H)pyrimidinedione was 2.2 grams. The NMR spectrum was consistent with the proposed structure.

Step E Synthesis of 3-(2-chloro-6-fluorobenzothiazol-7-yl)-1-methyl-6-trifluoromethyl-2,4-(1H,3H)pyrimidinedione (compound 10)

This compound was prepared in the manner of Step F, the alternate method, Example 1, with 2.2 grams (6.0 mmole) of 3-(2-chloro-6-fluorobenzothiazol-7-yl)-6-trifluoromethyl-2,4-(1H,3H)pyrimidinedione, 1.4 grams (10 mmole) of potassium carbonate, 1.4 grams (10 mmole) of iodomethane, and 50 mL of acetone as reagents. The yield of 3-(2-chloro-6-fluorobenzothiazol-7-yl)-1-methyl-6-trifluoromethyl-2,4-(1H,3H)pyrimidinedione was 1.3 grams, m.p. 69°–71° C. The NMR spectrum was consistent with the proposed structure.

EXAMPLE 8

Synthesis of 3-(2-chloro-6-fluorobenzothiazol-7-yl)-1-methyl-5-chloro-6-trifluoromethyl-2,4-(1H,3H)-pyrimidinedione (Compound 11)

Under a nitrogen atmosphere a stirred solution of 0.6 gram of (1.5 mmole) of 3-(2-chloro-6-fluorobenzothiazol-7-yl)-1-methyl-6-trifluoromethyl-2,4-(1H,3H) pyrimidinedione (prepared by way of Example 7), 0.24 gram (1.8 mmole) of N-chlorosuccinimide, 15 mL of N,N-dimethylformamide, and 0.1 mL acetic acid was heated at 65° C. for 24 hours. After this time the reaction mixture was cooled to ambient temperature and poured into 150 mL of aqueous 5% sodium bicarbonate. To this was added 10 grams of solid lithium chloride. The reaction mixture was then stirred for ten minutes. The resulting precipitate was collected by filtration and dried to give 0.42 gram of a white solid, which was purified by column chromatography on silica gel. Elution was accomplished using 6:1 hexane:ethyl acetate. The product-containing fractions were combined and concentrated under reduced pressure, yielding 0.26 gram of 3-(2-chloro-6-fluorobenzothiazol-7-yl)-1-methyl-5-chloro-6-trifluoromethyl-2,4-(1H,3H)pyrimidinedione, m.p. 81°–83° C. The NMR spectrum indicated that the material was 3-(2-chloro-6-fluorobenzothiazol- 7-yl)-1-methyl-5-chloro-6-trifluoromethyl-2,4-(1H,3H)pyrimidinedione rather than 3-(2,4-dichloro-6-fluorobenzothiazol-7-yl)-1-methyl-6-trifluoromethyl-2,4-(1H,3H)pyrimidinedione.

EXAMPLE 9

Synthesis of 3-(2-methylthio-4-chlorobenzothiazol-7-yl)-1-methyl-6-trifluoromethyl-2,4-(1H,3H)-pyrimidinedione (Compound 8)

Step A Synthesis of 7-amino-2-methylthio-4-chlorobenzothiazole as an Intermediate Under a nitrogen atmosphere a stirred solution of 0.88 gram (4 mmole) of 7-amino-2,4-dichlorobenzothiazole, 1.2 grams (17 mmole) of sodium thiomethoxide, and 25 mL of N,N-dimethylformamide was heated at 60° C. for two hours. The reaction mixture was cooled, poured into 150 mL of cold 5% sodium bicarbonate, and 50 mL of saturated sodium chloride solution was added. The resulting precipitate was filtered and vaccuum dried, yielding 0.8 grams of a yellow green solid. NMR analysis indicated this material was half 7-amino-2,4-dichlorobenzothiazole starting material and half the desired product 7-amino-2-methylthio-4-chlorobenzothiazole.

The reaction was repeated with 2.3 grams (10.5 mmole) of 7-amino-2,4-dichlorobenzothiazole, 1.2 grams (17 mmole) of sodium thiomethoxide, and 25 mL of N,N-dimethylformamide as reagents. After the reaction mixture had been heated for two hours at 60° C. the 0.8 grams from the previous reaction was added, and the reaction mixture was heated for an additional three hours. The reaction mixture was cooled and poured into 300 mL of cold aqueous sodium bicarbonate solution. To this was then added 10 grams of solid lithium chloride. The reaction mixture was extracted with three 100 mL portions of diethyl ether. The combined organic extracts were washed with an aqueous saturated sodium chloride solution. The organic layer was dried with sodium sulfate, filtered, and concentrated under reduced pressure, yielding 2.0 grams of 7-amino-2-methylthio-4-chlorobenzothiazole. The NMR spectrum was consistent with the proposed structure.

Step B Synthesis of ethyl N-(2-methylthio-4-chlorobenzothiazol-7-yl) carbamate as an Intermediate This compound was prepared in the manner of Step C, Example 7, with 2.0 grams (8.7 mmole) of 7-amino-2-methylthio-4-chlorobenzothiazole, 40 mL pyridine, and 1.84 grams (17 mmole) of ethyl chloroformate as reagents. The yield of ethyl N-(2-methylthio-4-chlorobenzothiazol-7-yl) carbamate was 2.4 grams. The NMR spectrum was consistent with the proposed structure.

Step C Synthesis of 3-(2-methylthio-4-chlorobenzothiazol-7-yl)-6-trifluoromethyl-2,4-(1H,3H)pyrimidinedione as an Intermediate This compound was prepared in the manner of Step E, Example 1, with 1.8 grams (5.9 mmole) of ethyl N-(2-methylthio-4-chlorobenzothiazol-7-yl)carbamate, 1.3 grams (7.0 mmole) of ethyl 3-amino-4,4,4-trifluorocrotonate, 0.35 gram (6.5 mmole) of sodium methoxide, 25 mL of N,N-dimethylformamide, and 0.76 gram (5 mmole) of 1,8-diazabicyclo[5.4.0]undec-7-ene as reagents. The yield of 3-(2-methylthio-4-chlorobenzothiazol-7-yl)-6-trifluoromethyl-2,4-(1H,3H)pyrimidinedione was 0.9 gram. The NMR spectrum was consistent with the proposed structure.

Step D Synthesis of 3-(2-methylthio-4-chlorobenzothiazol-7-yl)-1-methyl-6-trifluoromethyl-2,4-(1H,3H)pyrimidinedione (compound 8)

This compound was prepared in the manner of Step F, the alternative method, Example 1, with 0.90 gram (2.3 mmole) of 3-(2-methylthio-4-chlorobenzothiazol-7-yl)-6-trifluoromethyl-2,4-(1H,3H)pyrimidinedione, 0.48 gram (3.5 mmole) of potassium carbonate, 0.50 gram (3.5 mmole) of iodomethane, and 20 mL of acetone as reagents. The yield of 3-(2-methylthio-4-chlorobenzothiazol-7-yl)-1-methyl-6-trifluoromethyl-2,4-(1H,3H)pyrimidinedione was 0.6 gram, m.p. 79°–81° C. The NMR spectrum was consistent with the proposed structure.

EXAMPLE 10

Synthesis of 3-(4-methoxy-2,6-dichlorobenzothiazol-7-yl)-1-methyl-6-trifluoromethyl-2,4-(1H,3H)-pyrimidinedione (Compound 18)

Step A Synthesis of 2,6-dichloro-7-nitrobenzothiazole as an Intermediate

This compound was prepared in the manner of Step D, Example 6, with 8.0 grams (39 mmole) of 2,6-dichlorobenzothiazole, 45 mL of concentrated sulfuric acid, and 3.8 mL (60 mmole) of concentrated nitric acid as reagents. The material was purified by column chromatography on silica gel. Elution was accomplished with 3:1 heptane:ethyl acetate. The product-containing fractions were combined and concentrated under reduced pressure, yielding 2,6-dichloro-7 nitrobenzothiazole. The NMR spectrum was consistent with the proposed structure.

Step B Synthesis of 7-amino-2,6-dichlorobenzothiazole as an Intermediate

This compound was prepared in the manner of Step E, Example 6, with 9.5 grams (33 mmole) of 2,6-dichloro-7-nitrobenzothiazole, 4.5 grams (80 mmole) of iron powder, 30 mL of acetic acid, 150 mL of ethanol, and 3.3 mL (40 mmole) of concentrated hydrochloric acid as reagents. The yield of 7-amino-2,6-dichlorobenzothiazole was 6.0 grams. The NMR spectrum was consistent with the proposed structure.

Step C Synthesis of 7-amino-2,4,6-trichlorobenzothiazole as an Intermediate

Under a nitrogen atmosphere a solution of 6.0 grams (27 mmole) of 7-amino-2,6-dichlorobenzothiazole in 75 mL of N,N-dimethylformamide was stirred and cooled in an ice bath. To this was then added 4.3 grams (32 mmole) of N-chlorosuccinimide. Upon completion of the addition the reaction mixture was stirred for 20 minutes and then warmed to ambient temperature and stirred for an additional 18 hours. After this time the reaction mixture was poured into 250 mL of ice-water, and about 15 grams of lithium chloride was added, after which the reaction mixture was stirred for 30 minutes. The resulting precipitate was collected by filtration and dried under reduced pressure, yielding a dark solid, which was purified by column chromatography on silica gel. Elution was accomplished with 4:1 hexane:ethyl acetate. The product-containing fractions were combined and concentrated under reduced pressure, yielding 4.4 grams of 7-amino-2,4,6-trichlorobenzothiazole. The NMR spectrum was consistent with the proposed structure.

Step D Synthesis of (2,4,6-trichlorobenzothiazol-7-yl) isocyanate as an Intermediate Under a nitrogen atmosphere 25 mL of ethyl acetate was stirred and cooled in an ice bath. To this was added via syringe 9.5 mL (18 mmole) of 1.9M phosgene in toluene. During 25 minutes, a solution of 3.0 grams (11.8 mmole) of 7-amino-2,4,6-trichlorobenzothiazole in 75 mL of ethyl acetate was added dropwise. Upon completion of the addition the reaction mixture was warmed to ambient temperature and then gently heated at reflux for 2.5 hours. After this time the reaction mixture was concentrated under reduced pressure, yielding (2,4,6-trichlorobenzothiazol-7-yl) isocyanate, which was stored in a refrigerator.

Step E Synthesis of 3-(2,4,6-trichlorobenzothiazol-7-yl)-6-trifluoromethyl-2,4-(1H,3H)pyrimidinedione as an Intermediate This compound was prepared in the manner of Step E, Example 1, with 2.5 grams (8.9 mmole) of (2,4,6-trichlorobenzothiazol-7-yl)isocyanate, 1.8 grams (10 mmole) of ethyl 3-amino-4,4,4-trifluorocrotonate, 0.59 gram (11 mmole) of sodium methoxide, 50 mL of N,N-dimethylformamide, and 1.5 grams (9 mmole) of 1,8-diazabicyclo[5.4.0]undec-7-ene as reagents. The yield of 3-(2,4,6-trichlorobenzothiazol-7-yl)-6-trifluoromethyl-2,4-(1H,3H)-pyrimidinedione was 0.8 gram. The NMR spectrum was consistent with the proposed structure.

Step F Synthesis of 3-(4-methoxy-2,6-dichlorobenzothiazol-7-yl)-1-methyl-6-trifluoromethyl-2,4-(1H,3H) pyrimidinedione (45Compound 18)

This compound was prepared in the manner of Step F, the alternative method, Example 1, with 0.70 gram (1.8 mmole) of 3-(2,4,6-trichlorobenzothiazol-7-yl)-6-trifluoromethyl-2,4-(1H,3H)pyrimidinedione, 0.5 gram (3.6 mmole) of potassium carbonate, 0.51 gram (3.6 mmole) of iodomethane, and 30 mL of acetone as reagents. The yield of 3-(4-methoxy-2,6-dichlorobenzothiazol-7-yl)-1-methyl-6-trifluoromethyl-2,4-(1H,3H)pyrimidinedione was 0.3 gram, m.p. 185°–187° C. The NMR spectrum indicated that the material was 3-(4-methoxy-2,6-dichlorobenzothiazol-7-yl)-1-methyl-6-trifluoromethyl-2,4-(1H,3H)pyrimidinedione rather than 3-(2,4,6-trichlorobenzothiazol-7-yl)-1-methyl-6-trifluoromethyl-2,4-(1H,3H)pyrimidinedione, which was the intended compound.

EXAMPLE 11

Synthesis of 3-(2-methyl-4-chloro-6-fluorobenzothiazol-7-yl)-1-methyl-6-trifluoromethyl-2,4-(1H,3H)-pyrimidinedione (Compound 12)

Step A Synthesis of 2-methyl-6-fluoro-7-nitrobenzothiazole as an Intermediate

This compound was prepared in the manner of Step D, Example 6, with 9.3 grams (55 mmole) of 2-methyl-6-fluorobenzothiazole, 50 mL of concentrated sulfuric acid, and 4.2 mL (67 mmole) of concentrated nitric acid as reagents. The material was purified by column chromatography on silica gel. Elution was accomplished with 3:1 heptane:ethyl acetate. The product-containing fractions were combined and concentrated under reduced pressure. The yield of 2-methyl-6-fluoro-7-nitrobenzothiazole was 5.7 grams. The NMR spectrum was consistent with the proposed structure.

Step B Synthesis of 7-amino-2-methyl-6-fluorobenzothiazole as an Intermediate

This compound was prepared in the manner of Step E, Example 6, with 7.0 grams (33 mmole) of 2-methyl-6-fluoro-7-nitrobenzothiazole, 7.0 grams (125 mmole) of iron powder, 30 mL of acetic acid, and 75 mL of ethanol as reagents. The yield of 7-amino-2-methyl-6-fluorobenzothiazole was 5.1 grams. The NMR spectrum was consistent with the proposed structure.

Step C Synthesis of ethyl N-(2-methyl-6-fluorobenzothiazol-7-yl) carbamate as an Intermediate This compound was prepared in the manner of Step C, Example 7, with 5.0 grams (27 mmole) of 7-amino-2-methyl-6-fluorobenzothiazole, 50 mL pyridine, and 5.4 grams (50 mmole) of ethyl chloroformate as reagents. This preparation differs in that the ethyl chloroformate was added to the 7-amino-2-methyl-6-fluorobenzothiazole/pyridine solution rather than the 7-amino-2-methyl-6-fluorobenzothiazole/pyridine solution being added to the ethyl chloroformate. The material was purified by recrystallization from 5:1 petroleum ether and chloroform. The yield of ethyl N-(2-methyl-6-fluorobenzothiazol-7-yl) carbamate was 3.5 grams, m.p. 132°–134° C. The NMR spectrum was consistent with the proposed structure.

Step D Synthesis of ethyl N-(2-methyl-4-chloro-6-fluorobenzothiazol-7-yl)carbamate as an Intermediate This compound was prepared in the manner of Step D, Example 1, with 2.5 grams (9.8 mmole) of ethyl N-(2-methyl-6-fluorobenzothiazol-7-yl)carbamate, 1.6 grams (10 mmole) of N,N-dichlorourethane, 0.17 mL (2.0 mmole) of concentrated hydrochloric acid, and 35 mL of acetic acid as reagents. The yield of ethyl N-(2-methyl-4-chloro-6-fluorobenzothiazol-7-yl)carbamate was 2.2 grams, m.p. 167°–169° C. The NMR spectrum was consistent with the proposed structure.

Step E Synthesis of 3-(2-methyl-4-chloro-6-fluorobenzothiazol-7-yl)-6-trifluoromethyl-2,4-(1H,3H) pyrimidinedione as an Intermediate This compound was prepared in the manner of Step E, Example 1, with 1.8 grams (6.2 mmole) of ethyl N-(2-methyl-4-chloro-6-fluorobenzothiazol-7-yl)carbamate, 1.25 grams (6.8 mmole) of ethyl 3-amino-4,4,4-trifluorocrotonate, 0.35 gram (6.5 mmole) of sodium methoxide, 50 mL of N,N-dimethylformamide, and 0.94 gram (6.2 mmole) of 1,8-diazabicyclo[5.4.0]-undec- 7-ene as reagents. The yield of 3-(2-methyl-4-chloro-6-fluorobenzothiazol-7-yl)-6-trifluoromethyl-2,4-(1H,3H) pyrimidinedione was 1.25 grams. The NMR spectrum was consistent with the proposed structure.

Step F Synthesis of 3-(2-methyl-4-chloro-6-fluorobenzothiazol-7-yl)-1-methyl-6-trifluoromethyl-2,4-(1H,3H)pyrimidinedione (Compound 12)

This compound was prepared in the manner of Step F, Example 1, with 0.55 gram (1.4 mmole) of 3-(2-methyl-4-chloro-6-fluorobenzothiazol-7-yl)-6-trifluoromethyl-2,4-(1H,3H)pyrimidinedione, 0.34 gram (2.5 mmole) of potassium carbonate, 0.35 gram (2.5 mmole) of iodomethane, and 25 mL of acetone as reagents. The yield of 3-(2-methyl-4-chloro-6-fluorobenzothiazol-7-yl)-1-methyl-6-trifluoromethyl-2,4-(1H,3H)pyrimidinedione was 0.45 gram, m.p. 83°–85° C. The NMR spectrum was consistent with the proposed structure.

EXAMPLE 12

Synthesis of 3-[2-(1-piperidinyl)-4-chloro-6-fluorobenzothiazol-7-yl]- 1-methyl-6-trifluoromethyl-2,4-(1H,3H)pyrimidinedione (Compound 15)

Step A Synthesis of ethyl N-(2,4-dichloro-6-fluorobenzothiazol-7-yl) carbamate as an Intermediate This compound was prepared in the manner of Step D, Example 1, with 3.6 grams (13.1 mmole) of ethyl N-(2-chloro-6-fluorobenzothiazol-7-yl)carbamate (prepared as in Steps A–D, Example 7), 2.2 grams (14.0 mmole) of N,N-dichlorourethane, 0.1 7 mL (2.0 mmole) of concentrated hydrochloric acid, and 100 mL of acetic acid as reagents. The yield of ethyl N-(2,4-dichloro-6-fluorobenzothiazol-7-yl)carbamate was 3.1 grams. The NMR spectrum was consistent with the proposed structure.

Step B Synthesis of ethyl N-[2-(1-piperidinyl)-4-chloro-6-fluorobenzothiazol-7-yl]carbamate as an Intermediate Under a nitrogen atmosphere a solution of 3.0 grams (9.7 mmole) of ethyl N-(2,4-dichloro-6-fluorobenzothiazol-7-yl) carbamate in 75 mL of tetrahydrofuran was stirred, and 1.7 grams (20 mmole) of piperidine was added. Upon completion of the addition the reaction mixture was stirred for 1.5 hours at ambient temperature. The reaction mixture was then poured into a mixture of 75 mL of aqueous 10% ammonium chloride and 75 mL of an aqueous saturated sodium chloride solution. The resulting mixture was extracted with three 75 mL portions of ethyl acetate. The combined extracts were washed with two 50 mL portions of an aqueous saturated sodium chloride solution. The organic layer was dried with sodium sulfate, filtered, and the filtrate was concentrated under reduced pressure, yielding a brown solid, which was purified by column chromatography on silica gel. Elution was accomplished with 2:1 heptane:ethyl acetate. The product-containing fractions were combined and concentrated, yielding 2.6 grams of ethyl N-[2-(1-piperidinyl)-4-chloro-6-fluorobenzothiazol-7-yl]carbamate. The NMR spectrum was consistent with the proposed structure.

Step C Synthesis of 3-[2-(1-piperidinyl)-4-chloro-6-fluorobenzothiazol-7-yl]-6-trifluoromethyl-2,4-(1H,3H) pyrimidinedione as an Intermediate This compound was prepared in the manner of Step E, Example 1, with 2.2 grams (6.1 mmole) of ethyl N-[2-(1-piperidinyl)-4-chloro-6-fluorobenzothiazol-7-yl]carbamate, 1.3 grams (7.0 mmole) of ethyl 3-amino-4,4,4-trifluorocrotonate, 0.38 gram (7.0 mmole) of sodium methoxide, 50 mL of N,N-dimethylformamide, and 0.93 gram (6.1 mmole) of 1,8-diazabicyclo[5.4.0]undec-7-ene as reagents. The yield of 3-[2-(1-piperidinyl)-4-chloro-6-fluorobenzothiazol-7-yl]-6-trifluoromethyl-2,4-(1H,3H) pyrimidinedione was 0.75 gram. The NMR spectrum was consistent with the proposed structure.

Step D Synthesis of 3-[2-(1-piperidinyl)-4-chloro-6-fluorobenzothiazol-7-yl]-1-methyl-6-trifluoromethyl-2,4-(1H,3H)pyrimidinedione (Compound 15)

This compound was prepared in the manner of Step F, the alternative method, Example 1, with 0.7 gram (1.6 mmole) of 3-[2-(1-piperidinyl)-4-chloro-6-fluorobenzothiazol-7-yl]-6-trifluoromethyl-2,4-(1H,3H)pyrimidinedione, 0.41 gram (3.0 mmole) of potassium carbonate, 0.43 gram (3.0 mmole) of iodomethane, and 45 mL of acetone as reagents. The yield of 3-[2-(1-piperidinyl)-4-chloro-6-fluorobenzothiazol-7-yl]-1-methyl-6-trifluoromethyl-2,4-(1H,3H)pyrimidinedione was 0.5 gram. The NMR spectrum was consistent with the proposed structure.

EXAMPLE 13

Synthesis of 3-[2-(1-piperidinyl)-4-chlorobenzothiazol-7-yl]-1-methyl-6-trifluoromethyl-2,4-(1H,3H)-pyrimidinedione (Compound 9)

Step A Synthesis of 2-(1-piperidinyl)-4-chloro-7-nitrobenzothiazole as an Intermediate Under a nitrogen atmosphere a solution of 1.7 grams (6.8 mmole) of 2,4-dichloro-7-nitrobenzothiazole in 150 mL of diethyl ether was stirred as 1.2 grams (13.7 mmole) of piperidine was added via syringe over a ten minute period. The reaction mixture, which had spontaneously warmed, was cooled with ice-water to ambient temperature, where it stirred for 40 minutes. The resulting precipitate was collected by filtration and washed with 50 mL of ethyl acetate. The filtrate was washed with aqueous 0.1N hydrochloric acid and two 50 mL portions of water. The organic layer was dried with sodium sulfate, filtered, and concentrated under reduced pressure, yielding a bright yellow-orange solid, which was combined with a material prepared by a similar route and purified by column chromatography on silica gel. Elution was accomplished with 7:1 followed by 5:1 hexane:ethyl acetate. The product-containing fractions were combined and concentrated under reduced pressure, yielding 1.3 grams of 2-(1-piperidinyl)-4-chloro-7-nitrobenzothiazole. The NMR spectrum was consistent with the proposed structure.

Step B Synthesis of 7-amino-2-(1-piperidinyl)-4-chlorobenzothiazole as an Intermediate This compound was prepared in the manner of Step E, Example 6, with 1.2 grams (4.0 mmole) of 2-(1-piperidinyl)-4-chloro-7-nitrobenzothiazole, 0.89 gram (16.0 mmole) of iron powder, 0.33 mL (4 mmole) of concentrated hydrochloric acid, 2 mL of acetic acid, and 50 mL of ethanol as reagents. The yield of 7-amino-2-(1-piperidinyl)-4-chlorobenzothiazole was 1.1 grams. The NMR spectrum was consistent with the proposed structure.

Step C Synthesis of ethyl N-[2-(1-piperidinyl)-4-chlorobenzothiazol-7-yl]carbamate as an Intermediate This compound was prepared in the manner of Step C, Example 7, with 1.0 gram (3.7 mmole) of 7-amino-2-(1-piperidinyl)-4-chlorobenzothiazole, 20 mL pyridine, and 0.76 gram (7.0 mmole) of ethyl chloroformate as reagents. The yield of ethyl N-[2-(1-piperidinyl)-4-chlorobenzothiazol-7-yl]carbamate was 1.6 grams. The NMR spectrum was consistent with the proposed structure.

Step D Synthesis of 3-[2-(1-piperidinyl)-4-chlorobenzothiazol-7-yl]-6-trifluoromethyl-2,4-(1H,3H) pyrimidinedione as an Intermediate This compound was prepared in the manner of Step E, Example 1, with 1.3 grams (3.8 mmole) of ethyl N-[2-(1-piperidinyl)-4-chlorobenzothiazol-7-yl]carbamate, 0.77 gram (4.2 mmole) of ethyl 3-amino-4,4,4-trifluorocrotonate, 0.22 gram (4.1 mmole) of sodium methoxide, 25 mL of N,N-dimethylformamide, and 0.5 mL (3.3 mmole) of 1,8-diazabicyclo[5.4.0]undec-7-ene as reagents. The yield of 3-[2-(1-piperidinyl)-4-chlorobenzothiazol-7-yl]-6-trifluoromethyl-2,4-(1H,3H)pyrimidinedione was 0.68 gram. The NMR spectrum was consistent with the proposed structure.

Step E Synthesis of 3-[2-(1-piperidinyl)-4-chlorobenzothiazol-7-yl]-1-methyl-6-trifluoromethyl-2,4-(1H,3H)pyrimidinedione (Compound 9)

This compound was prepared in the manner of Step F, the alternative method, Example 1, with 0.66 gram (1.6 mmole) of 3-[2-(1-piperidinyl)-4-chlorobenzothiazol-7-yl]-6-trifluoromethyl-2,4-(1H,3H)pyrimidinedione, 0.33 gram (2.4 mmole) of potassium carbonate, 0.43 gram (3.0 mmole) of iodomethane, and 25 mL of acetone as reagents. The yield of 3-[2-(1-piperidinyl)-4-chlorobenzothiazol-7-yl]-1-methyl-6-trifluoromethyl-2,4-(1H,3H)-pyrimidinedione was 0.3 gram, m.p. 102°–104° C. The NMR spectrum was consistent with the proposed structure.

EXAMPLE 14

Synthesis of 3-(2-dibromomethyl-4-chloro-6-fluorobenzoxazol-7-yl)-1-methyl-6-trifluoromethyl-2,4-(1H,3H)-pyrimidinedione (Compound 56)

A stirred solution of 1.6 grams (4.2 mmole) of 3-(2-methyl-4-chloro-6-fluorobenzoxazol-7-yl)-1-methyl-6-trifluoromethyl-2,4-(1H,3H)pyrimidinedione, 5.0 grams (28 mmole) of N-bromosuccinimide, 0.05 gram (0.3 mmole) of 2,2'-azobis(2-methylpropionitrile), and 0.05 gram (0.2 mmole) of benzoyl peroxide in 50 mL of carbon tetrachloride was heated to reflux, where it stirred for 32 hours. After this time the reaction mixture was allowed to cool to ambient temperature, where it stirred for about an additional 48 hours. At the conclusion of this period 50 mL of trichloromethane was added, and the resulting precipitate was collected by filtration and washed with one 20 mL portion of trichloromethane. The combined filtrate and wash were concentrated under reduced pressure to a yellow solid, which was subjected to column chromatography on silica gel. Elution was with 5:1 followed by 2:1 heptane and ethyl acetate. The product-containing fractions were combined and concentrated under reduced pressure, yielding 0.15 gram of 3-(2-dibromomethyl-4-chloro-6-fluorobenzoxazol-7-yl)-1-methyl-6-trifluoromethyl-2,4-(1H,3H) pyrimidinedione. The NMR spectrum was consistent with the proposed structure. This 0.15 gram of product was combined with 0.39 gram of product prepared by a similar route, yielding a total of 0.54 gram of 3-(2-dibromomethyl-4-chloro-6-fluorobenzoxazol-7-yl)-1-methyl-6-trifluoromethyl-2,4-(1H,3H)pyrimidinedione, m.p. 144°–146° C.

EXAMPLE 15

Synthesis of 3-[2-(1-hydroxy-1-methylethyl)-4-chloro-6-fluorobenzoxazol-7-yl)-1-methyl-6-trifluoromethyl-2,4-(1H,3H)pyrimidinedione (Compound 58)

Step A Synthesis of N-(3-chloro-4-fluorophenyl)-2-methoxy-2-methylpropionamide as an Intermediate A stirred solution of 6.1 grams (42 mmole) of 3-chloro-4-fluoroaniline, 5.0 grams (42 mmole) of 2-methoxy-2-methylpropanoic acid, and 10.5 grams (55 mmole) of 1-(3-dimethylaminopropyl)-3-ethylcarbodiimide hydrochloride in 120 mL of methylene chloride was cooled to about 0° C., and 7.4 grams (55 mmole) of 1-hydroxybenzotriazole was added. Upon completion of the addition the reaction was slowly warmed to ambient temperature, where it stirred for about 18 hours. After this time the reaction mixture was poured into water, and the resulting mixture was filtered through diatomaceous earth to remove any salts that had precipitated. The organic layer was separated from the aqueous layer, washed with an aqueous saturated sodium chloride solution, dried with sodium sulfate, and filtered. The filtrate was concentrated under reduced pressure to a brown oil, which was passed through a silica gel scrub plug, yielding 5.0 grams of N-(3-chloro-4-fluorophenyl)-2-methoxy-2-methylpropionamide. The NMR spectrum was consistent with the proposed structure.

Step B Synthesis of [2-(1-methoxy-1-methylethyl)-6-fluorobenzoxazol-7-yl]carboxylic acid as an Intermediate This compound was prepared in the manner of Step B, Example 1, with 4.9 grams (20 mmole) of N-(3-chloro-4-fluorophenyl)-2-methoxy-2-methylpropionamide, 120 mL of tetrahydrofuran, 17.6 mL (44 mmole) of 2.5M n-butyllithium in hexanes, and 3.0 grams of solid carbon dioxide as reagents. The yield of [2-(1-methoxy-1-methylethyl)-6-fluorobenzoxazol-7-yl]carboxylic acid was 3.5 grams. The NMR spectrum was consistent with the proposed structure.

An additional 2.1 grams of [2-(1-methoxy-1-methylethyl)-6-fluorobenzoxazol-7-yl]carboxylic acid of was prepared in the manner of Step B, Example 1, with 4.2 grams (17 mmole) of N-(3-chloro-4-fluorophenyl)-2-methoxy-2-methylpropionamide, 120 mL of tetrahydrofuran, 16 mL (40 mmole) of 2.5M n-butyllithium in hexanes, and 3.0 grams of solid carbon dioxide as reagents. The NMR spectrum was consistent with the proposed structure.

Step C Synthesis of [2-(1-methoxy-1-methylethyl)-6-fluorobenzoxazol-7-yl]carbonyl azide as an Intermediate This compound was prepared in the manner of Step C, Example 1, with 5.6 grams (22 mmole) of [2-(1-methoxy-1-methylethyl)-6-fluorobenzoxazol-7-yl]carboxylic acid, 30 mL of tetrahydrofuran, 2.3 grams (22.7 mmole) of 4-methylmorpholine, 2.2 mL (27 mmole) of ethyl chloroformate, 3.0 grams (45 mmole) of sodium azide, and 3 mL of water as reagents. The yield of [2-(1-methoxy-1-methylethyl)-6-fluorobenzoxazol-7-yl]carbonyl azide was 3.7 grams. The NMR spectrum was consistent with the proposed structure.

Step D Synthesis of ethyl N-[2-(1-methoxy-1-methylethyl)-6-fluorobenzoxazol-7-yl]carbamate as an Intermediate Under a nitrogen atmosphere a stirred solution of 3.7 grams (13 mmole) of [2-(1-methoxy-1-methylethyl)-6-fluorobenzoxazol-7-yl]carbonyl azide in 25 mL of ethanol was heated to reflux where it stirred for about 18 hours. After this time the reaction mixture was cooled to ambient temperature, and the ethanol was removed, yielding a yellow oil, which was subjected to column chromatography on silica gel. Elution was with 4:1 heptane and ethyl acetate. The product-containing fractions were combined and concentrated under reduce pressure, yielding 2.5 grams of ethyl N-[2-(1-methoxy-1-methylethyl)-6-fluorobenzoxazol-7-yl] carbamate. The NMR spectrum was consistent with the proposed structure.

Step E Synthesis of ethyl N-[2-(1-methoxy-1-methylethyl)-4-chloro-6-fluorobenzoxazol-7-yl]carbamate as an Intermediate This compound was prepared in the manner of Step D, Example 1, with 2.5 grams (8.8 mmole) of ethyl N-[2-(1-methoxy-1-methylethyl)-6-fluorobenzoxazol-7-yl] carbamate, 30 mL of acetic acid, about 0.5 mL (6 mmole) of concentrated hydrochloric acid, and 1.4 grams (8.8 mmole) of N,N-dichlorourethane as reagents. The yield of ethyl N-[2-(1-methoxy-1-methylethyl)-4-chloro-6-fluorobenzoxazol-7-yl]carbamate was 2.2 grams, m.p. 95°–97° C. The NMR spectrum was consistent with the proposed structure.

Step F Synthesis of 3-[2-(1-methoxy-1-methylethyl)-4-chloro-6-fluorobenzoxazol-7-yl)-6-trifluoromethyl-2,4-(1H,3H)pyrimidinedione as an Intermediate This compound was prepared in the manner of Step E, Example 1, with 0.8 gram (2.4 mmole) of ethyl N-[2-(1-methoxy-1-methylethyl)-4-chloro-6-fluorobenzoxazol-7-yl] carbamate, 0.15 gram (2.8 mmole) of sodium methoxide, 0.44 gram (2.4 mmole) of ethyl 3-amino-4,4,4-trifluorocrotonate, 30 mL of N,N-dimethylformamide, and 0.37 gram (2.4 mmole) of 1,8-diazabicyclo-[5.4.0]undec-7-ene as reagents. The yield of 3-[2-(1-methoxy-1-methylethyl)-4-chloro-6-fluorobenzoxazol-7-yl)-6-trifluoromethyl-2,4-(1H,3H)-pyrimidinedione was 0.3 gram. The NMR spectrum was consistent with the proposed structure.

An additional 0.6 gram of 3-[2-(1-methoxy-1-methylethyl)-4-chloro-6-fluorobenzoxazol-7-yl)-6-trifluoromethyl-2,4-(1H,3H)pyrimidinedione was prepared in the manner of Step E, Example 1, with 0.8 gram (2.4 mmole) of ethyl N-[2-(1-methoxy-1-methylethyl)-4-chloro-6-fluorobenzoxazol-7-yl]carbamate, 0.15 gram (2.8 mmole) of sodium methoxide, 0.44 gram (2.4 mmole) of ethyl 3-amino-4,4,4-trifluorocrotonate, 30 mL of N,N-dimethylformamide, arid 0.37 gram (2.4 mmole) of 1,8-diazabicyclo[5.4.0]undec-7-ene as reagents. The NMR spectrum was consistent with the proposed structure.

Step G Synthesis of 3-[2-(1-methoxy-1-methylethyl)-4-chloro-6-fluorobenzoxazol-7-yl)-1-methyl-6-trifluoromethyl-2,4-(1H,3H)-pyrimidinedione as an Intermediate This compound was prepared in the manner of Step F, Example 1, with 0.6 gram (1.4 mmole) of 3-[2-(1-methoxy-1-methylethyl)-4-chloro-6-fluorobenzoxazol-7-yl)-6-trifluoromethyl-2,4-(1H,3H)pyrimidinedione, 0.39 gram (2.8 mmole) of potassium carbonate, 0.4 gram (2.8 mmole) of methyl iodide, and 15 mL of acetone as reagents. The yield of 3-[2-(1-methoxy-1-methylethyl)-4-chloro-6-fluorobenzoxazol-7-yl)-1-methyl-6-trifluoromethyl-2,4-(1H,3H)pyrimidinedione was 0.6 gram. The NMR spectrum was consistent with the proposed structure.

Step H Synthesis of 3-[2-(1-hydroxy-1-methylethyl)-4-chloro-6-fluorobenzoxazol-7-yI)-1-methyl-6-trifluoromethyl-2,4-(1H,3H)-pyrimidinedione (Compound 58)

Under a nitrogen atmosphere a stirred solution of 3.8 mL (3.8 mmole) of 1M boron tribromide (in methylene chloride) in 50 mL of methylene chloride was cooled to about –40° C., and a solution of 0.6 gram (2.6 mmole) of 3-[2-(1-methoxy-1-methylethyl)-4-chloro-6-fluorobenzoxazol-7-yl)-1-methyl-6-trifluoromethyl-2,4-(1H,3H)pyrimidinedione in 50 mL of methylene chloride was added dropwise at such a rate as to maintain the reaction mixture temperature below –30° C. Upon completion of the addition the reaction mixture was allowed to warm to ambient temperature, where it stirred for about 18 hours. At the conclusion of this period the reaction mixture was poured into water and thoroughly extracted with methylene chloride. The combined extracts were washed with an aqueous saturated sodium chloride solution, dried with sodium sulfate, and filtered. The filtrate was concentrated under reduced pressure to a brown oil, which was subjected to column chromatography on silica gel. Elution was with 1:4 ethyl acetate to heptane. The product-containing fractions were combined and concentrated under reduced pressure, yielding 0.3 gram of 3-[2-(1-hydroxy-1-methylethyl)-4-chloro-6-fluorobenzoxazol-7-yl)-1-methyl-6-trifluoromethyl-2,4-(1H,3H)-pyrimidinedione. The NMR spectrum was consistent with the proposed structure.

EXAMPLE 16

Synthesis of 3-(2-thio-4-chloro-6-fluorobenzoxazol-7-yl)-1-methyl-6-trifluoromethyl-2,4-(1H,3H) pyrimidinedione (Compound 53)

Step A Synthesis of ethyl N-(4-chloro-2,6-difluorophenyl) carbamate as an Intermediate This compound was prepared in the manner of Step A, Example 6, with 26.9 grams (165 mmole) of 4-chloro-2,6-dilfuoroaniline and 17.4 mL (182 mmole) of ethyl chloroformate in 90 mL of pyridine as reagents. The yield of ethyl N-(4-chloro-2,6-difluorophenyl)carbamate was 23.6 grams. The NMR spectrum was consistent with the proposed structure.

Step B Synthesis of ethyl N-(4-chloro-2,6-difluoro-3-nitrophenyl)carbamate as an Intermediate This compound was prepared in the manner of Step D, Example 6, with 23.6 grams (109 mmole) of ethyl N-(4-chloro-2,6-difluorophenyl)carbamate and 7.7 mL (123 mmole) of 70% nitric acid in 125 mL of sulfuric acid as reagents. The yield of ethyl N-(4-chloro-2,6-difluoro-3-nitrophenyl)carbamate is 30.6 grams. The NMR spectrum was consistent with the proposed structure.

Step C Synthesis of ethyl N-(4-chloro-6-fluoro-2-methoxy-3-nitrophenyl)carbamate as an Intermediate Under a nitrogen atmosphere a solution of 30.6 grams (109 mmole) of ethyl N-(4-chloro-2,6-difluoro-3-nitrophenyl)carbamate and 18 mL (449 mmole) of methanol in 175 mL of dioxane was stirred, and 218 mL (218 mmole) of 1M sodium trimethylsilanoate (in tetrahydrofuran) was added dropwise during a 45 minute period. Upon completion of the addition the reaction mixture was heated to 65° C., where it stirred for three hours. At the conclusion of this period the reaction mixture was allowed to cool to ambient temperature, where it stirred for about 18 hours. The reaction mixture was concentrated under reduced pressure to a residue, which was taken up in cold 3N hydrochloric acid. The resulting solid was collected by filtration, washed with petroleum ether, and heat dried under vacuum, yielding 21.3 grams of ethyl N-(4-chloro-6-fluoro-2-methoxy-3-nitrophenyl)carbamate. The NMR spectrum was consistent with the proposed structure.

Step D Synthesis of ethyl N-(3-amino-4-chloro-6-fluoro-2-methoxyphenyl)carbamate as an Intermediate This compound was prepared in the manner of Step E, Example 6, with 21.3 grams (72 mmole) of ethyl N-(4-chloro-6-fluoro-2-methoxy-3-nitrophenyl)carbamate, 18.3 grams (328 mmole) of iron powder, 50 mL of acetic acid, 250 mL of ethanol, and 3 mL (36 mmole) of hydrochloric acid as reagents. This preparation differed in that the hydrochloric acid was added. The yield of ethyl N-(3-amino-4-chloro-6-fluoro-2-methoxyphenyl)carbamate was 15.0 grams. The NMR spectrum was consistent with the proposed structure.

Step E Synthesis of 3-(3-amino-4-chloro-6-fluoro-2-methoxyphenyl)-6-trifluoromethyl-2,4-(1H,3H) pyrimidinedione as an Intermediate This compound was prepared in the manner of Step E, Example 1, with 15.0 grams (57 mmole) of ethyl N-(3-amino-4-chloro-6-fluoro-2-methoxy-phenyl)carbamate, 3.6 grams (66 mmole) of sodium methoxide, and 10.5 grams (57 mmole) of ethyl 3-amino-4,4,4-trifluorocrotonate in 100 mL of N,N-dimethylformamide as reagents. This preparation differed in that no 1,8-diazabicyclo[5.4.0]undec-7-ene was added. The yield of 3-(3-amino-4-chloro-6-fluoro-2-methoxyphenyl)-6-trifluoromethyl-2,4-(1H,3H) pyrimidinedione was 10.0 grams. The NMR spectrum was consistent with the proposed structure.

Step F Synthesis of 3-(3-amino-4-chloro-6-fluoro-2-methoxyphenyl)-1-methyl-6-trifluoromethyl-2,4-(1H,3H) pyrimidinedione as an Intermediate This compound was prepared in the manner of Step F, Example 1, with 10.0 grams (28 mmole) of 3-(3-amino-4-chloro-6-fluoro-2-methoxyphenyl)-6-trifluoromethyl-2,4-(1H,3H)pyrimidinedione, 5.7 grams (41 mmole) of potassium carbonate, 26 mL (41 mmole) of methyl iodide, and 70 mL of acetone as reagents. The yield of 3-(3-amino-4-chloro-6-fluoro-2-methoxy-phenyl)-1-methyl-6-trifluoromethyl-2,4-(1H,3H)pyrimidinedione was 7.3 grams. The NMR spectrum was consistent with the proposed structure.

Step G Synthesis of 3-(3-amino-4-chloro-6-fluoro-2-hydroxy)-1-methyl-6-trifluoromethyl-2,4-(1H,3H) pyrimidinedione as an Intermediate This compound was prepared in the manner of Step H, Example 15, with 7.3 grams (20 mmole) of 3-(3-amino-4-chloro-6-fluoro-2-methoxyphenyl)-1-methyl-6-trifluoromethyl-2,4-(1H,3H)pyrimidinedione and 80 mL (80 mmole) of 1M boron tribromide (in methylene chloride) in 120 mL of methylene chloride as reagents. The yield of 3-(3-amino-4-chloro-6-fluoro-2-hydroxy)-1-methyl-6-trifluoromethyl-2,4-(1H,3H)pyrimidinedione was 5.4 grams. The NMR spectrum was consistent with the proposed structure.

Step H Synthesis of 3-(2-thio-4-chloro-6-fluorobenzoxazol-7-yl)-1-methyl-6-trifluoromethyl-2,4-(1H,3H) pyrimidinedione (compound 53)

Under a nitrogen atmosphere a stirred solution of 5.4 grams (15 mmole) of 3-(3-amino-4-chloro-6-fluoro-2-hydroxy)-1-methyl-6-trifluoromethyl-2,4-(1H,3H)

pyrimidinedione and 4.9 grams (30 mmole) of potassium ethyl xanthate in 25 mL of ethanol was heated at reflux for four hours. After this time the reaction mixture was cooled to ambient temperature and concentrated under reduced pressure to a residue, which was taken up in water and acidified to pH 5 with acetic acid. The resulting mixture was thoroughly extracted with methylene chloride. The combined extracts were washed with an aqueous saturated sodium chloride solution, dried with sodium sulfate, and filtered. The filtrate was concentrated under reduced pressure to a brown oil, which was subjected to column chromatography on silica gel. Elution was with 1:3 followed by 1:1 ethyl acetate to heptane. The product-containing fractions were combined and concentrated under reduced pressure, yielding 1.0 gram of crude product. This crude product was purified by column chromatography on silica gel. Elution was with 1:9 methanol and methylene chloride. The product-containing fractions were combined and concentrated under reduced pressure, yielding 0.3 gram of 3-(2-thio-4-chloro-6-fluorobenzoxazol-7-yl)-1-methyl-6-trifluoromethyl-2,4-(1H,3H)pyrimidinedione. The NMR spectrum was consistent with the proposed structure.

EXAMPLE 17

Synthesis of 3-(2-methylthio-4-chloro-6-fluorobenzoxazol-7-yl)-1-methyl-6-trifluoromethyl-2,4-(1H,3H)-pyrimidinedione (compound 51)

This compound was prepared in the manner of Step F, Example 1, with 4.0 grams (10 mmole) of 3-(2-thio-4-chloro-6-fluorobenzoxazol-7-yl)-1-methyl-6-trifluoromethyl-2,4-(1H,3H)pyrimidinedione, 1.5 grams (11 mmole) of potassium carbonate, 1.7 grams (12 mmole) of methyl iodide, and 25 mL of acetone as reagents. The yield of 3-(2-methylthio-4-chloro-6-fluorobenzoxazol-7-yl)-1-methyl-6-trifluoromethyl-2,4-(1H,3H)-pyrimidinedione was 0.4 gram. The NMR spectrum was consistent with the proposed structure.

EXAMPLE 18

Synthesis of 3-(2-amino-4-chloro-6-fluorobenzoxazol-7-yl)-1-methyl-6-trifluoromethyl-2,4-(1H,3H)pyrimidinedione (Compound 70)

A stirred solution of 1.3 grams (3.5 mmole) of 3-(3-amino-4-chloro-6-fluoro-2-hydroxy)-1-methyl-6-trifluoromethyl-2,4-(1H,3H)pyrimidinedione in 20 mL of methanol was cooled to about 0° C. in an ice bath and 0.4 gram (3.5 mmole) of cyanogen bromide was added dropwise during a ten minute period. At the conclusion of this period the reaction mixture was warmed to ambient temperature, where it stirred for about 18 hours. The reaction mixture was poured into an aqueous saturated sodium bicarbonate solution. The resulting mixture was thoroughly extracted with portions of ethyl acetate. The combined extracts were washed with an aqueous saturated sodium chloride solution, dried with sodium sulfate, and filtered. The filtrate was concentrated under reduced pressure to a dark oil, which was subjected to column chromatography on silica gel. Elution was with 1:50 methanol and methylene chloride. The product-containing fractions were combined and concentrated under reduced pressure to yield the crude product, which was purified by recrystallization from methylene chloride. The yield of 3-(2-amino-4-chloro-6-fluorobenzoxazol-7-yl)-1-methyl-6-trifluoromethyl-2,4-(1H,3H)pyrimidinedione was 0.5 grams, m.p. 144°–150° C. The NMR spectrum was consistent with the proposed structure.

EXAMPLE 19

Synthesis of 3-(2-ethoxyacetyl-4-chloro-6-fluorobenzoxazol-7-yl)-1-methyl-6-trifluoromethyl-2,4-(1H,3H)-pyrimidinedione (compound 93)

Step A Synthesis of 3-[5-(ethylmalonylamino)-6-(ethylmalonyloxy)-4-chloro-2-fluorophenyl]-1-methyl-6-trifluoromethyl-2,4-(1H,3H)-pyrimidinedione as an Intermediate Under a nitrogen atmosphere a stirred solution of 1.2 grams (8.4 mmole) of phosphorus pentoxide and 3.2 grams (20 mmole) of hexamethyldisiloxane was heated to 80° C., and a solution of 1.5 grams (4.2 mmole) of 3-(3-amino-4-chloro-6-fluoro-2-hydroxy)-1-methyl-6-trifluoromethyl-2,4-(1H,3H)pyrimidinedione and 1.0 gram (6 mmole) of the potassium salt of ethyl malonate in 50 mL of dioxane was added. Upon completion of the addition the reaction mixture was heated to reflux, where it stirred for 16 hours. After this time the reaction mixture was cooled to ambient temperature and poured into 100 mL of water. The resulting mixture was extracted with three 50 mL portions of ethyl acetate. The extracts were combined and washed with two 50 mL portions of an aqueous saturated sodium chloride solution. The combined extracts and washes were dried with magnesium sulfate and filtered. The filtrate was concentrated under reduced pressure, yielding 2.6 grams of a yellow oil. The NMR spectrum indicated that the yellow oil was 3-[5-(ethylmalonylamino)-6-(ethylmalonyloxy)-4-chloro-2-fluorophenyl]-1-methyl-6-trifluoromethyl-2,4-(1H,3H) pyrimidinedione rather than 3-(2-ethoxyacetyl-4-chloro-6-fluorobenzoxazol-7-yl)-1-methyl-6-trifluoromethyl-2,4-(1H,3H)pyrimidinedione.

Step B Synthesis of 3-(2-ethoxyacetyl-4-chloro-6-fluorobenzoxazol-7-yl)-1-methyl-6-trifluoromethyl-2,4-(1H,3H)pyrimidinedione (compound 93)

This compound was prepared in the manner of Step G, Example 6, with 2.6 grams (4.4 mmole) of 3-[5-(ethylmalonylamino)-6-(ethylmalonyloxy)-4-chloro-2-fluorophenyl]-1-methyl-6-trifluoromethyl-2,4-(1H,3H) pyrimidinedione, 1.2 grams (8.4 mmole) of phosphorus pentoxide, and 3.2 grams (20 mmole) of hexamethyldisiloxane in 30 mL of toluene as reagents. This preparation differed in that toluene was used rather than acetic acid. The yield of 3-(2-ethoxyacetyl-4-chloro-6-fluorobenzoxazol-7-yl)-1-methyl-6-trifluoromethyl-2,4-(1H,3H) pyrimidinedione was 0.5 gram, m.p. 56°–58° C. The NMR spectrum was consistent with the proposed structure.

EXAMPLE 20

Synthesis of 3-(2-acetylamino-4-chloro-6-fluorobenzoxazol-7-yl)-1-methyl-6-trifluoromethyl-2,4-(1H,3H)-pyrimidinedione (compound 115)

A solution of 3.8 grams (10 mmole) of 3-(2-amino-4-chloro-6-fluorobenzoxazol-7-yl)-1-methyl-6-trifluoromethyl-2,4-(1H,3H)pyrimidinedione and 1.0 gram (15 mmole) of acetyl chloride in 20 mL of pyridine is stirred at ambient temperature for about 18 hours. The reaction mixture is concentrated under reduced pressure, yielding 3-(2-acetylamino-4-chloro-6-fluorobenzoxazol-7-yl)-1-methyl-6-trifluoromethyl-2,4-(1H,3H)pyrimidinedione.

EXAMPLE 21

Synthesis of 3-[2-(N-acetyl-N-methylsulfonylamino)-4-chloro-6-fluorobenzoxazol-7-yl]-1-methyl-6-trifluoromethyl-2,4-(1H,3H) pyrimidinedione (compound 116)

A stirred suspension of 2.0 grams (51 mmole) of 60% sodium hydride (in mineral oil) in 25 mL of tetrahydrofuran is cooled in an ice bath. To this is added a solution of 10.2 grams (25.5 mmole) of 3-(2-acetylamino-4-chloro-6-fluorobenzoxazol-7-yl)-1-methyl-6-trifluoromethyl-2,4-(1H,3H)pyrimidinedione in 25 mL of tetrahydrofuran. Upon completion of the addition 2.9 grams (25.3 mmole) of methanesulfonyl chloride is added. The reaction mixture is heated to reflux, where it stirs for one hour and then concentrated under reduced pressure, yielding 3-[2-(N-acetyl-N-methylsulfonylamino)-4-chloro-6-fluorobenzoxazol-7-yl]-1-methyl-6-trifluoromethyl-2,4-(1H,3H)-pyrimidinedione.

EXAMPLE 22

Synthesis of 3-(2-methylsulfonylamino-4-chloro-6-fluorobenzoxazol-7-yl)-1-methyl-6-trifluoromethyl-2,4-(1H,3H)pyrimidinedione (compound 71)

A stirred solution of 4.5 grams (10 mmole) of 3-[2-(N-acetyl-N-methylsulfonylamino)-4-chloro-6-fluorobenzoxazol-7-yl]-1-methyl-6-trifluoromethyl-2,4-(1H,3H)pyrimidinedione in 25 mL of 85% hydrazine is heated to 60° C., where it stirs for about 18 hours. After this time the reaction mixture is concentrated under reduced pressure, yielding 3-(2-methylsulfonylamino-4-chloro-6-fluorobenzoxazol-7-yl)-1-methyl-6-trifluoromethyl-2,4-(1H,3H)-pyrimidinedione.

The 3-(2-methylsulfonylamino-4-chloro-6-fluorobenzoxazol-7-yl)- 1-methyl-6-trifluoromethyl-2,4-(1H,3H)pyrimidinedione can also be prepared in the manner stated above with 3N hydrochloric acid rather than hydrazine and by heating at reflux rather than 60° C.

EXAMPLE 23

Synthesis of 3-[2-(N-methyl-N-methylsulfonylamino)-4-chloro-6-fluorobenzoxazol-7-yl]-1-methyl-6-trifluoromethyl-2,4-(1H,3H) pyrimidinedione (compound 76)

This compound is prepared in the manner of Step F, Example 1, with 4.3 grams (10 mmole) of 3-(2-methylsulfonylamino-4-chloro-6-fluorobenzoxazol-7-yl)-1-methyl-6-trifluoromethyl-2,4-(1H,3H)pyrimidinedione, 1.5 grams (11 mmole) of potassium carbonate, 1.7 grams (12 mmole) of methyl iodide, and 25 mL of acetone as reagents.

EXAMPLE 24

Synthesis of 3-(2,4-dichloro-6-fluorobenzoxazol-7-yl)-1-methyl-6-trifluoromethyl-2,4-(1H,3H) pyrimidinedione (compound 106)
Step A Synthesis of 3-(2-oxo-4-chloro-6-fluoro-2,3-dihydrobenzoxazol-7-yl)-1-methyl-6-trifluoromethyl-2,4-(1H,3H)pyrimidine dione as an Intermediate Under a nitrogen atmosphere a stirred solution of 0.7 gram (4.3 mmole) of 1,1'-carbonyldiimidazole and 1.0 gram (2.8 mmole) of 3-(3-amino-4-chloro-6-fluoro-2-hydroxy)-1-methyl-6-trifluoromethyl-2,4-(1H,3H)pyrimidinedione in 30 mL of tetrahydrofuran was heated to reflux, where it stirred for 1.5 hours, then cooled to ambient temperature, where it stirred for about 18 hours. After this time the reaction mixture was poured into 1N aqueous hydrochloric acid. The resulting mixture was thoroughly extracted with portions of ethyl acetate. The combined extracts were washed with portions of an aqueous saturated sodium chloride solution, dried with magnesium sulfate, and filtered. The filtrate was concentrated under reduced pressure, yielding 1.0 gram of 3-(2-oxo-4-chloro-6-fluoro-2,3-dihydrobenzoxazol-7-yl)-1-methyl-6-trifluoromethyl-2,4-(1H,3H)pyrimidinedione, m.p. 67°–71° C. The NMR spectrum was consistent with the proposed structure.
Step B Synthesis of 3-(2,4-dichloro-6-fluorobenzoxazol-7-yl)-1-methyl-6-trifluoromethyl-2,4-(1H,3H) pyrimidinedione (compound 106)

A stirring solution of 3.8 grams (10 mmole) of 3-(2-oxo-4-chloro-6-fluoro-2,3-dihydrobenzoxazol-7-yl)-1-methyl-6-trifluoromethyl-2,4-(1H,3H)pyrimidinedione and 7.7 grams (50 mmole) of phosphorus oxychloride is cooled in an ice bath. To this 5.0 grams (49.4 mmole) of triethylamine is added via syringe during a ten minute period. At the conclusion of this period the reaction mixture is heated to reflux where it stirs for four hours. After this period the reaction mixture is cooled to ambient temperature and poured into ice water. The resulting mixture is extracted with portions of diethyl ether. The extracts are combined, washed with an aqueous saturated sodium bicarbonate solution, dried with sodium sulfate, and filtered. The filtrate is concentrated under reduced pressure, yielding 3-(2,4-dichloro-6-fluorobenzoxazol-7-yl)-1-methyl-6-trifluoromethyl-2,4-(1H,3H)pyrimidinedione.

EXAMPLE 25

Synthesis of 3-(4-chloro-6-fluoro-2-phenoxybenzoxazol-7-yl]-1-methyl-6-trifluoromethyl-2,4-(1H,3H)pyrimidinedione (compound 118)

Under a nitrogen atmosphere, a stirred solution of 2.0 grams (51 mmole) of 60% sodium hydride (in mineral oil) in 25 mL of N,N-dimethylformamide is cooled in an ice bath, and a solution of 5.3 grams (56.3 mmoles) of phenol in 25 mL of N,N-dimethylformamide is added dropwise during a five minute period. To this is added a solution of 20.3 grams (51 mmole) of 3-(2,4-dichloro-6-fluorobenzoxazol-7-yl)-1-methyl-6-trifluoromethyl-2,4-(1H,3H)pyrimidinedione (as prepared in Example 24) in 25 mL of N,N-dimethylformamide. Upon completion of the addition the reaction mixture is allowed to warm to ambient temperature, where it stirs for about 18 hours. After this time the reaction mixture is concentrated under reduced pressure, yielding 3-(4-chloro-6-fluoro-2-phenoxybenzoxazol-7-yl]-1-methyl-6-trifluoromethyl-2,4-(1H,3H)pyrimidinedione.

Novel intermediates used in the preparation of the compounds described above include compounds of the formula:

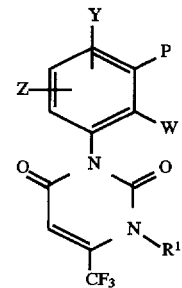

in which: P is nitro, amino, or azido; W is hydrogen, alkoxy, or hydroxy; $R^1$ is hydrogen, lower alkyl, or amino; X is oxygen; Y is hydrogen, hydrogen, halogen, alkoxy, or nitro; Z is halogen; and P and W together may be —N—C(O)—O— to complete a benzoxazole ring.

HERBICIDAL ACTIVITY

The 3-(substituted benzoxazol-7-yl) and 3-(substituted benzothiazol-7-yl)-1-substituted-6-trifluoromethyl-2,4-(1H, 3H)pyrimidinediones of the present invention were tested for pre- and postemergence herbicidal activity on a variety of crops and weeds. The test plants included soybean (*Glycine max* var. Winchester), field corn (*Zea mays* var. Pioneer 3732), wheat (*Triticum aestivum* var. Lew), morningglory (*Ipomea lacunosa* or *Ipomea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium strumarium* L.).

For preemergence testing, two disposable fiber flats (8 cm ×15 cm ×25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepare in the same manner except that they were planted 9–14 days prior to the preemergence flats and were placed in a greenhouse and watered, thus allowing the seeds to germinate and the foliage to develop.

In both pre- and postemergence tests, a stock solution of the candidate herbicide was prepared by dissolving 0.27 g of the compound in 20 mL of water/acetone (50/50) containing 0.5% v/v sorbitan monolaurate. For an application rate of 3 g/ha of herbicide a 0.10 mL portion of the stock solution was diluted with water/acetone (50/50) to 45.01 mL.

The preemergence flats were initially subjected to a light water spray. The four flats were placed two by two along a conveyor belt (i.e., the two preemergence followed by the two postemergence flats). The conveyor belt passed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced, and once the spray stabilized, the flats were passed under the spray at a speed to receive a coverage equivalent of 1000 L/ha, affording the rate of 3 g/ha. The preemergence flats were watered immediately thereafter, placed in the greenhouse, and watered regularly at the soil surface. The postemergence flats were immediately placed in the greenhouse and not watered until 24 hours after treatment with the test solution. Thereafter they were regularly watered at ground level. After 12–17 days the plants were examined and the phytotoxicity data were recorded.

Herbicidal activity data are given for various compounds of the present invention in Table 3 (preemergence) and Table 4 (postemergence). The test compounds are identified by numbers that correspond to those in Table 1.

Phytotoxicity data are taken as percent control. Percent control is determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| Herbicide Rating System | | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the 3-(substituted benzoxazol-7-yl) and 3-(substituted benzothiazol-7-yl)-1-substituted-6-trifluoromethyl-2,4-(1H,3H)-pyrimidinediones are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and postemergence herbicides, are in the form of finely divided particles which disperse readily in water or other dispersants. The wettable powder is ultimately applied to the soil either as a dry dust or as an emulsion in water or other liquid. Typical carriers for wettable powders include Fuller's earth, kaolin clays, silicas, and other highly absorbent, readily wettable inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, 1.0 part of sodium lignosulfonate, and 0.3 part of sulfonated aliphatic polyester as wetting agents. Frequently, additional wetting agent and/or oil will be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylphenyl sulfonates and sulfates and their sodium salts; alkylphenyl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form by a propellant, such as carbon dioxide, propane or butane, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The 3-(substituted benzoxazol-7-yl) and 3-(substituted benzothiazol-7-yl)-1-substituted-6-trifluoromethyl-2,4-(1H, 3H)pyrimidinediones of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, for example, about 4 to 300 g/ha to, preferably, about 10 to 30 g/ha. For field use, where there are losses of herbicide, higher application rates (for example, four times the rates mentioned above) may be employed.

The 3-(substituted benzoxazol-7-yl) and 3-(substituted benzothiazol-7-yl)-1-substituted-6-trifluoromethyl-2,4-(1H, 3H)pyrimidinediones of this invention may be used in combination with other herbicides, for example they may be mixed with, say, an equal or larger amount of a known herbicide such as aryloxyalkanoic acid herbicides such as (2,4-dichlorophenoxy)acetic acid (2,4-D), (4-chloro-2-methylphenoxy)acetic acid (MCPA), (+/−)-2-(4-chloro-2-methylphenoxy)propanoic acid (MCPP); urea herbicides, such as N,N-dimethyl-N'-[4-(1-methylethyl)phenyl]urea (isoproturon); imidazolinone herbicides, such as 2-[4,5-dihydro-4-methyl-4-(1-methylethyl)-5-oxo- 1H-imidazol-2-yl]-3-pyridinecarboxylic acid (imazapyr), a reaction product comprising (+/−)-2-[4,5-dihydro-4-methyl-4-(1-methylethyl)-5-oxo-1H-imidazol-2-yl]-4-methylbenzoic acid and (+/−)-2-[4,5-dihydro-4-methyl-4-(1-methylethyl)-5-oxo-1H-imidazol-2-yl]-5-methylbenzoic acid (imazamethabenz), (+/−)-2-[4,5-dihydro-4-methyl-4-(1-methylethyl)-5-oxo-1H-imidazol-2-yl]-5-ethyl-3-pyridinecarboxylic acid (imazethapyr),and (+/−)-2-[4,5-dihydro-4-methyl-4-(1-methylethyl)-5-oxo- 1H-imidazol-2-yl]-3-quinolinecarboxylic acid (imazaquin); diphenyl ether herbicides, such as 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil); sulfonylurea herbicides, such as 2-[[[[(4-chloro-6-methoxy-2-pyrimidinyl)amino]carbonyl]amino] sulfonyl]-benzoic acid (chlorimuron), 2-chloro-N-[[(4-methoxy-6-methyl-1,3,5-triazin-2-yl)amino]carbonyl] benzenesulfonamide (chlorsulfuron), 2-[[[[[(4,6-dimethoxy-2-pyrimidinyl)amino]carbonyl]amino]sulfonyl]methyl] benzoic acid (bensulfuron), 2-[[[[(4,6-dimethoxy-2-pyrimidinyl)amino]carbonyl]amino]-sulfonyl]-1-methyl-1H-pyrazol-4-carboxylic acid (pyrazosulfuron), 3-[[[[(4-methoxy-6-methyl-1,3,5-triazin-2-yl)amino]carbonyl] amino]sulfonyl]-2-thiophenecarboxylic acid (thifensulfuron), and 2-(2-chloroethoxy)-N-[[(4-methoxy-6- methyl-1,3,5-triazin-2-yl)amino]carbonyl]benzenesulfonamide (triasulfuron); 2-(4-aryloxyphenoxy) alkanoic acid herbicides, such as (+/−)-2-[4-[(6-chloro-2-benzoxazolyl)oxy]phenoxy]propanoic acid (fenoxaprop), (+/−)-2-[4-[[5-(trifluoromethyl)-2-pyridinyl]oxy]phenoxy] propanoic acid (fluazifop), (+/−)-2-[4-(6-chloro-2-quinoxalinyl)oxy]phenoxy]propanoic acid (quizalofop), and (+/−)-2-[-(2,4-dichlorophenoxy)phenoxy]propanoic acid (diclofop); benzothiadiazone herbicides, such as 3-(1-methylethyl)-1H-2,1,3-benzothiadiazin-4(3H)-one 2,2-dioxide (bentazone); 2-chloroacetanilide herbicides, such as N-(butoxymethyl)-2-chloro-2',6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

TABLE 1

HERBICIDAL 3-SUBSTITUTED-1-SUBSTITUTED-6-TRIFLUORO-METHYL-2,4-(1H,3H)PYRIMIDINEDIONES

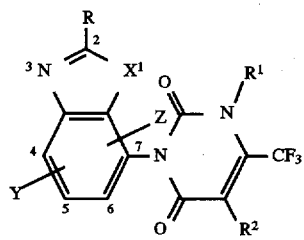

| Cmpd. No. | R | $R^1$ | $R^2$ | X | Y | Z |
|---|---|---|---|---|---|---|
| 1 | t-butyl | —$CH_3$ | H | O | H | 4-Cl |
| 2 | t-butyl | —$CH_3$ | Cl | O | H | 4-Cl |
| 3 | t-butyl | —$NH_2$ | H | O | H | 4-Cl |
| 4 | t-butyl | —$CH_3$ | H | O | 4-Cl | 6-F |
| 5 | t-butyl | —$NH_2$ | H | O | 4-Cl | 6-F |
| 6 | —$CH_3$ | —$CH_3$ | H | O | 4-Cl | 6-F |
| 7 | Cl | —$CH_3$ | H | S | H | 4-Cl |
| 8 | —$SCH_3$ | —$CH_3$ | H | S | H | 4-Cl |
| 9 | —N(piperidinyl) | —$CH_3$ | H | S | H | 4-Cl |
| 10 | Cl | —$CH_3$ | H | S | H | 6-F |
| 11 | Cl | —$CH_3$ | Cl | S | H | 6-F |
| 12 | —$CH_3$ | —$CH_3$ | H | S | 4-Cl | 6-F |
| 13 | isopropyl | —$CH_3$ | H | S | 4-Cl | 6-F |
| 14 | —$NHC_4H_9$ | —$CH_3$ | H | S | 4-Cl | 6-F |
| 15 | —N(piperidinyl) | —$CH_3$ | H | S | 4-Cl | 6-F |
| 16 | —$CH_3$ | —$CH_3$ | H | S | H | 4-Cl |
| 17 | n-propyl | —$CH_3$ | H | S | H | 4-Cl |
| 18 | Cl | —$CH_3$ | H | S | 4-$OCH_3$ | 6-Cl |
| 19 | isobutyl | —$CH_3$ | H | O | 4-Cl | 6-F |
| 20 | —$CH_2OCH_3$ | —$CH_3$ | H | O | 4-Cl | 6-F |
| 21 | —$CH_2Cl$ | —$CH_3$ | H | O | 4-Cl | 6-F |
| 22 | phenyl | —$CH_3$ | H | O | 4-Cl | 6-F |
| 23 | isopropyl | —$CH_3$ | H | O | 4-Cl | 6-F |
| 24 | benzyl | —$CH_3$ | H | O | 4-Cl | 6-F |
| 25 | —$CH_3$ | —$CH_3$ | H | O | 4-Cl | 6-Cl |
| 26 | hexyl | —$OH_3$ | H | O | 4-Cl | 6-F |
| 27 | —$C(CH_3)_2CH_2Cl$ | —$CH_3$ | H | O | 4-Cl | 6-F |
| 28 | t-butyl | —$CH_3$ | H | O | 4-Cl | 6-Cl |
| 29 | —CH(H)(4-Cl-phenyl) | —$CH_3$ | H | O | 4-Cl | 6-F |

TABLE 1-continued

HERBICIDAL 3-SUBSTITUTED-1-SUBSTITUTED-6-TRIFLUORO-
METHYL-2,4-(1H,3H)PYRIMIDINEDIONES

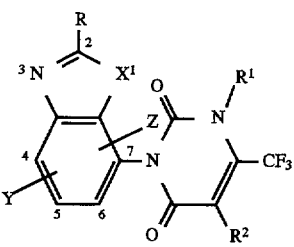

| Cmpd. No. | R | $R^1$ | $R^2$ | X | Y | Z |
|---|---|---|---|---|---|---|
| 30 | -CH(H)-(3-Cl-phenyl) | -CH$_3$ | H | O | 4-Cl | 6-F |
| 31 | -CH(H)-(4-Cl-phenyl) | -CH$_3$ | H | O | 4-Cl | 6-F |
| 32 | t-butyl | -CH$_3$ | H | O | 4-Br | 6-F |
| 33 | t-butyl | -CH$_3$ | H | O | 4-NO$_2$ | 6-F |
| 34 | -CH(H)-(2-OCH$_3$-phenyl) | -CH$_3$ | H | O | 4-Cl | 6-F |
| 35 | -CH(H)-(3-OCH$_3$-phenyl) | -CH$_3$ | H | O | 4-Cl | 6-F |
| 36 | -CH(H)-(4-OCH$_3$-phenyl) | -CH$_3$ | H | O | 4-Cl | 6-F |
| 37 | -C(CH$_3$)(CH$_3$)-CH$_2$-CH$_3$ | -CH$_3$ | H | O | 4-Cl | 6-F |
| 38 | -C(CH$_3$)(H)-phenyl | -CH$_3$ | H | O | 4-Cl | 6-F |
| 39 | -CH(H)-(3-CH$_3$-phenyl) | -CH$_3$ | H | O | 4-Cl | 6-F |

TABLE 1-continued

HERBICIDAL 3-SUBSTITUTED-1-SUBSTITUTED-6-TRIFLUORO-
METHYL-2,4-(1H,3H)PYRIMIDINEDIONES

| Cmpd. No. | R | R[1] | R[2] | X | Y | Z |
|---|---|---|---|---|---|---|
| 40 | 1-(3,5-dimethoxyphenyl)ethyl | —CH$_3$ | H | O | 4-Cl | 6-F |
| 41 | 1-(3,4-dimethoxyphenyl)ethyl | —CH$_3$ | H | O | 4-Cl | 6-F |
| 42 | 2-phenyl-2-propyl (cumyl) | —CH$_3$ | H | O | 4-Cl | 6-F |
| 43 | 1-(3,5-dimethoxyphenyl)-1-methylethyl | —CH$_3$ | H | O | 4-Cl | 6-F |
| 44 | 1-(3-trifluoromethylphenyl)ethyl | —CH$_3$ | H | O | 4-Cl | 6-F |
| 45 | t-butyl | —CH$_3$ | H | O | H | 6-F |
| 46 | 2-methoxyphenyl | —CH$_3$ | H | S | 4-Cl | 6-F |
| 47 | —SC$_3$H$_7$ | —CH$_3$ | H | S | 4-Cl | 6-F |
| 48 | —S(O)C$_3$H$_7$ | —CH$_3$ | H | S | 4-Cl | 6-F |
| 49 | —S(O)$_2$CH$_2$CH$_2$CH$_3$ | —CH$_3$ | H | S | 4-Cl | 6-F |
| 50 | isopropyl | —C—CN | H | S | 4-Cl | 6-F |
| 51 | —SCH$_3$ | —CH$_3$ | H | O | 4-Cl | 6-F |
| 52 | —SC$_2$H$_5$ | —CH$_3$ | H | O | 4-Cl | 6-F |
| 53 | —SH | —CH$_3$ | H | O | 4-Cl | 6-F |
| 54 | —SO$_2$CH$_3$ | —CH$_3$ | H | O | 4-Cl | 6-F |

TABLE 1-continued

HERBICIDAL 3-SUBSTITUTED-1-SUBSTITUTED-6-TRIFLUORO-
METHYL-2,4-(1H,3H)PYRIMIDINEDIONES

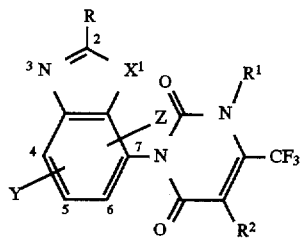

| Cmpd. No. | R | R¹ | R² | X | Y | Z |
|---|---|---|---|---|---|---|
| 55 | —CF₃ | —CH₃ | H | O | 4-Cl | 6-F |
| 56 | —CHBr₂ | —CH₃ | H | O | 4-Cl | 6-F |
| 57 | —CH₂Br | —CH₃ | H | O | 4-Cl | 6-F |
| 58 | —C(CH₃)(CH₃)OH | —CH₃ | H | O | 4-Cl | 6-F |
| 59 | —C(CH₃)(CH₃)O—CH₃ | —CH₃ | H | O | 4-Cl | 6-F |
| 60 | —C(CH₃)(CH₃)O—COCH₃ | —CH₃ | H | O | 4-Cl | 6-F |
| 61 | —C(CH₃)(CH₃)O—CO₂CH₃ | —CH₃ | H | O | 4-Cl | 6-F |
| 62 | —C(CH₃)(CH₂OH)OH | —CH₃ | H | O | 4-Cl | 6-F |
| 63 | —C(CH₃)(CH₂OCH₃)OCH₃ | —CH₃ | H | O | 4-Cl | 6-F |
| 64 | —C(CH₃)(CH₂OCOCH₃)COCH₃ | —CH₃ | H | O | 4-Cl | 6-F |
| 65 | —C(CH₃)(CH₂OCO₂CH₃)CO₂CH₃ | —CH₃ | H | O | 4-Cl | 6-F |
| 66 | ethyl | —CH₃ | H | O | 4-Cl | 6-F |
| 67 | n-propyl | —CH₃ | H | O | 4-Cl | 6-F |
| 68 | n-butyl | —CH₃ | H | O | 4-Cl | 6-F |
| 69 | sec-butyl | —CH₃ | H | O | 4-Cl | 6-F |
| 70 | —NH₂ | —CH₃ | H | O | 4-Cl | 6-F |
| 71 | —NHSO₂CH₃ | —CH₃ | H | O | 4-Cl | 6-F |
| 72 | —NHSO₂C₆H₅ | —CH₃ | H | O | 4-Cl | 6-F |
| 73 | —NHSO₂NHCH₃ | —CH₃ | H | O | 4-Cl | 6-F |
| 74 | —NHSO₂CH₂Cl | —CH₃ | H | O | 4-Cl | 6-F |
| 75 | —NHSO₂NHC₆H₅ | —CH₃ | H | O | 4-Cl | 6-F |
| 76 | —N(CH₃)SO₂CH₃ | —CH₃ | H | O | 4-Cl | 6-F |
| 77 | —N(C₂H₅)SO₂CH₃ | —CH₃ | H | O | 4-Cl | 6-F |
| 78 | —N(CH₂OCH₃)SO₂CH₃ | —CH₃ | H | O | 4-Cl | 6-F |
| 79 | —N(CH₂CH=CH₂)SO₂CH₃ | —CH₃ | H | O | 4-Cl | 6-F |
| 80 | —N(CH₂C≡CH)SO₂CH₃ | —CH₃ | H | O | 4-Cl | 6-F |

TABLE 1-continued

HERBICIDAL 3-SUBSTITUTED-1-SUBSTITUTED-6-TRIFLUORO-
METHYL-2,4-(1H,3H)PYRIMIDINEDIONES

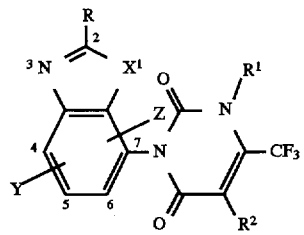

| Cmpd. No. | R | $R^1$ | $R^2$ | X | Y | Z |
|---|---|---|---|---|---|---|
| 81 | —N(CH₃)SO₂C₆H₅ | —CH₃ | H | O | 4-Cl | 6-F |
| 82 | —NHCH₂CO₂CH₃ | —CH₃ | H | O | 4-Cl | 6-F |
| 83 | —CO₂H | —CH₃ | H | O | 4-Cl | 6-F |
| 84 | —CO₂CH₃ | —CH₃ | H | O | 4-Cl | 6-F |
| 85 | —CO₂Na | —CH₃ | H | O | 4-Cl | 6-F |
| 86 | —CONH₂ | —CH₃ | H | O | 4-Cl | 6-F |
| 87 | —CONHCH₃ | —CH₃ | H | O | 4-Cl | 6-F |
| 88 | —CON(CH₃)₂ | —CH₃ | H | O | 4-Cl | 6-F |
| 89 | —CONHSO₂CH₃ | —CH₃ | H | O | 4-Cl | 6-F |
| 90 | —CO₂C₂H₅ | —CH₃ | H | O | 4-Cl | 6-F |
| 91 | ![structure: -C(=O)-O-CH(CH₃)-CH(CH₃)-H] | —CH₃ | H | O | 4-Cl | 6-F |
| 92 | —CH₂CO₂CH₃ | —CH₃ | H | O | 4-Cl | 6-F |
| 93 | —CH₂CO₂C₂H₅ | —CH₃ | H | O | 4-Cl | 6-F |
| 94 | —CH(CH₃)CO₂CH₃ | —CH₃ | H | O | 4-Cl | 6-F |
| 95 | —CH₂CH(Cl)CO₂CH₃ | —CH₃ | H | O | 4-Cl | 6-F |
| 96 | —CH₂CH(CH₃)CO₂CH₃ | —CH₃ | H | O | 4-Cl | 6-F |
| 97 | —CH=C(CH₃)CO₂CH₃ | —CH₃ | H | O | 4-Cl | 6-F |
| 98 | —CH=C(Cl)CO₂CH₃ | —CH₃ | H | O | 4-Cl | 6-F |
| 99 | —OCH₂CO₂CH₃ | —CH₃ | H | O | 4-Cl | 6-F |
| 100 | —OCH(CH₃)CO₂CH₃ | —CH₃ | H | O | 4-Cl | 6-F |
| 101 | —OCH₂CH=CH₂ | —CH₃ | H | O | 4-Cl | 6-F |
| 102 | —OCH₂C≡CH | —CH₃ | H | O | 4-Cl | 6-F |
| 103 | —OH | —CH₃ | H | O | 4-Cl | 6-F |
| 104 | —OCH₃ | —CH₃ | H | O | 4-Cl | 6-F |
| 105 | —OCH(CH₃)₂ | —CH₃ | H | O | 4-Cl | 6-F |
| 106 | Cl | —CH₃ | H | O | 4-Cl | 6-F |
| 107 | —SCH₂CO₂CH₃ | —CH₃ | H | O | 4-Cl | 6-F |
| 108 | —SCH₂CN | —CH₃ | H | O | 4-Cl | 6-F |
| 109 | —SCH₂C≡CH | —CH₃ | H | O | 4-Cl | 6-F |
| 110 | —SCH₂C₆H₅ | —CH₃ | H | O | 4-Cl | 6-F |
| 111 | —CH₂SCH₂CO₂CH₃ | —CH₃ | H | O | 4-Cl | 6-F |
| 112 | —CH₂SCH₂C₆H₅ | —CH₃ | H | O | 4-Cl | 6-F |
| 113 | —CH₂NHSO₂CH₃ | —CH₃ | H | O | 4-Cl | 6-F |
| 114 | —NHPO(OCH₃)₂ | —CH₃ | H | O | 4-Cl | 6-F |
| 115 | —NHCOCH₃ | —CH₃ | H | O | 4-Cl | 6-F |
| 116 | —N(SO₂CH₃)COCH₃ | —CH₃ | H | O | 4-Cl | 6-F |
| 117 | —CH₂OCH₂C≡CH | —CH₃ | H | O | 4-Cl | 6-F |
| 118 | —O—C₆H₅ | —CH₃ | H | O | 4-Cl | 6-F |
| 119 | —O—C₆H₄—C(=O)OCH₃ | —CH₃ | H | O | 4-Cl | 6-F |

TABLE 1-continued

HERBICIDAL 3-SUBSTITUTED-1-SUBSTITUTED-6-TRIFLUORO-METHYL-2,4-(1H,3H)PYRIMIDINEDIONES

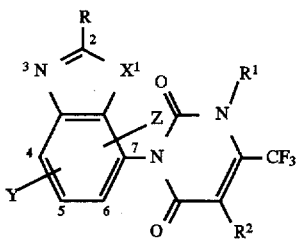

| Cmpd. No. | R | R¹ | R² | X | Y | Z |
|---|---|---|---|---|---|---|
| 120 | ![structure: -O-phenyl-O-CH(CH₃)-C(O)-OCH₃] | —CH₃ | H | O | 4-Cl | 6-F |
| 121 | ![structure: -O-phenyl-Cl] | —CH₃ | H | O | 4-Cl | 6-F |
| 122 | ![structure: -O-phenyl-CH₃] | —CH₃ | H | O | 4-Cl | 6-F |
| 123 | ![structure: -O-phenyl-CH₂-CHCl-C(O)-OCH₃] | —CH₃ | H | O | 4-Cl | 6-F |
| 124 | ![structure: -CH(H)-thiophene] | —CH₃ | H | O | 4-Cl | 6-F |

TABLE 2

CHARACTERIZING PROPERTIES

| Cmpd No | Melting Point (°C.) | Cmpd No | Melting Point (°C.) |
|---|---|---|---|
| 1 | 146–148 | 34 | oil |
| 2 | 83–86 | 35 | 50–54 |
| 3 | 104–106 | 36 | 170–175 |
| 4 | 68–70 | 37 | 63–66 |
| 5 | 90–92 | 38 | 60–63 |
| 6 | 64–66 | 39 | 55–60 |
| 7 | 86–88 | 40 | 137–139 |
| 8 | 79–81 | 41 | 58–62 |
| 9 | 102–104 | 42 | 183–186 |
| 10 | 59–61 | 43 | 50–58 |
| 11 | 81–83 | 44 | 59–63 |
| 12 | 83–85 | 45 | 144–146 |
| 13 | oil | 46 | 72–74 |
| 14 | 109–111 | 47 | 52–54 |
| 15 | 180–181 | 48 | 72–75 |
| 16 | 94–96 | 49 | 150–153 |
| 17 | 146–148 | 50 | 78–80 |
| 18 | 185–187 | 51 | 157–158 |
| 19 | 51–53 | 52 | 56° C. sublimes |
| 20 | 54–56 | 53 | 86° C. sublimes |
| 21 | 154–156 | 55 | 63–71 |
| 22 | 80–82 | 56 | 144–146 |
| 23 | 49–51 | 58 | 64–74 |
| 24 | low melting solid | 62 | 70–75 |
| 25 | 76–78 | 66 | 51–59 |
| 26 | oil | 67 | 43–50 |
| 27 | 65–69 | 68 | 47–51 |
| 28 | 64–67 | 69 | 50–54 |
| 29 | 50–52 | 70 | solid |
| 30 | 60–64 | 93 | 56–58 |
| 31 | 68–71 | 105 | 69–71 |
| 32 | 72–74 | 124 | 63–65 |

TABLE 3

PREEMERGENCE HERBICIDAL ACTIVITY (% CONTROL)

| | Compound No. | | | |
|---|---|---|---|---|
| | 1 | 2 | 3 | 4 |
| | Rate(kg/ha) | | | |
| | 0.3 | 0.3 | 0.3 | 0.3 |
| Species | | | | |
| Soybean | 100 | 100* | 100 | 100 |
| Wheat | 100 | 98* | 100 | 100 |
| Corn | 100 | 98* | 100 | 100 |
| Velvetleaf | 100 | 100* | 100 | 100 |
| Morningglory | 100 | 100* | 100 | 100 |
| Chickweed | 100 | 100* | 100 | 100 |
| Cocklebur | 100 | 90* | 100 | 100 |
| Blackgrass | 95 | 100* | 100 | 100 |
| Green foxtail | 100 | 100* | 100 | 100 |
| Johnsongrass | 100 | 100* | 100 | 100 |

| | Compound No. | | | |
|---|---|---|---|---|
| | 5 | 6 | 7 | 8 |
| | Rate(kg/ha) | | | |
| | 0.3 | 0.3 | 0.3 | 0.3 |
| Species | | | | |
| Soybean | 100 | 100 | 60 | 100 |
| Wheat | 95 | 100 | 50 | 80 |
| Corn | 100 | 100 | 70 | 90 |
| Velvetleaf | 100 | 100 | 100 | 100 |
| Morningglory | 100 | 100 | 100 | 95 |
| Chickweed | 100 | 100 | 100 | 100 |
| Cocklebur | 100 | 100 | 100 | 80 |
| Blackgrass | ND | 100 | 60 | 90 |
| Greenfoxtail | 100 | 100 | 100 | 100 |
| Johnsongrass | 100 | 100 | 100 | 100 |

| | Compound No. | | | |
|---|---|---|---|---|
| | 9 | 10 | 11 | 12 |
| | Rate(kg/ha) | | | |
| | 0.3 | 0.3 | 0.3 | 0.3 |
| Species | | | | |
| Soybean | 100 | 50 | 90 | 100 |
| Wheat | 85 | 30 | 20 | 100 |
| Corn | 95 | 70 | 70 | 100 |
| Velvetleaf | 100 | 100 | 100 | 100 |
| Morningglory | 100 | 90 | 70 | 100 |
| Chickweed | 100 | 50 | 0 | ND |
| Cocklebur | 50 | 90 | 40 | 100 |
| Blackgrass | 80 | 70 | 30 | ND |
| Greenfoxtail | 100 | 100 | 95 | 100 |
| Johnsongrass | 100 | 95 | 100 | 100 |

| | Compound No. | | | |
|---|---|---|---|---|
| | 13 | 14 | 15 | 16 |
| | Rate(kg/ha) | | | |
| | 0.3 | 0.3 | 0.3 | 0.3 |
| Species | | | | |
| Soybean | 100 | 100 | 100 | 100 |
| Wheat | 90 | 60 | 80 | 100 |
| Corn | 100 | 90 | 95 | 100 |
| Velvetleaf | 100 | 100 | 100 | 100 |
| Morningglory | 100 | 95 | 100 | 100 |
| Chickweed | 100 | 100 | 100 | 100 |
| Cocklebur | 100 | 50 | 100 | 100 |
| Blackgrass | ND | 60 | 95 | 100 |
| Green foxtail | 100 | 100 | 100 | 100 |
| Johnsongrass | 100 | 100 | 100 | 100 |

TABLE 3-continued

PREEMERGENCE HERBICIDAL ACTIVITY (% CONTROL)

| | Compound No. | | | |
|---|---|---|---|---|
| | 17 | 18 | 19 | 20 |
| | Rate(kg/ha) | | | |
| | 0.3 | 0.3 | 0.3 | 0.3 |
| Species | | | | |
| Soybean | 100 | 20 | 100 | 100 |
| Wheat | 100 | 50 | 80 | 100 |
| Corn | 100 | 60 | 90 | 100 |
| Velvetleaf | 100 | 100 | 100 | 100 |
| Morningglory | 100 | 90 | 100 | 100 |
| Chickweed | ND | 100 | 100 | 100 |
| Cocklebur | 100 | 10 | 100 | 100 |
| Blackgrass | 100 | 0 | 100 | 100 |
| Green foxtail | 100 | 100 | 100 | 100 |
| Johnsongrass | 100 | 40 | 100 | 100 |

| | Compound No. | | | |
|---|---|---|---|---|
| | 21 | 22 | 23 | 24 |
| | Rate(kg/ha) | | | |
| | 0.3 | 0.3 | 0.3 | 0.3 |
| Species | | | | |
| Soybean | 50 | 45 | 100 | 95 |
| Wheat | 60 | 30 | 100 | 50 |
| Corn | 60 | 50 | 100 | 80 |
| Velvetleaf | 100 | 100 | 100 | 100 |
| Morningglory | 100 | 100 | 100 | 100 |
| Chickweed | 80 | 95 | 100 | 100 |
| Cocklebur | 70 | 30 | 100 | 75 |
| Blackgrass | 50 | 75 | 100 | 90 |
| Green foxtail | 95 | 100 | 100 | 100 |
| Johnsongrass | 90 | 90 | 100 | 100 |

| | Compound No. | | | |
|---|---|---|---|---|
| | 25 | 26 | 27 | 28 |
| | Rate(kg/ha) | | | |
| | 0.3 | 0.3 | 0.3 | 0.3 |
| Species | | | | |
| Soybean | 100 | 100 | 100 | 95 |
| Wheat | 90 | 40 | 60 | 55 |
| Corn | 95 | 70 | 90 | 90 |
| Velvetleaf | 100 | 100 | 100 | 100 |
| Morningglory | 100 | 100 | 100 | 100 |
| Chickweed | 95 | 100 | 100 | 40 |
| Cocklebur | 70 | 100 | 80 | 40 |
| Blackgrass | 90 | 60 | 90 | 70 |
| Green foxtail | 100 | 100 | 100 | 100 |
| Johnsongrass | 100 | 60 | 100 | 100 |

Table 3 (first section, continued from above): Cocklebur 100 50 100 100; Blackgrass ND 60 95 100; Green foxtail 100 100 100 100; Johnsongrass 100 100 100 100.

TABLE 3-continued

PREEMERGENCE HERBICIDAL ACTIVITY (% CONTROL)

| | Compound No. | | | |
|---|---|---|---|---|
| | 29 | 30 | 31 | 32 |
| | Rate(kg/ha) | | | |
| | 0.3 | 0.3 | 0.3 | 0.3 |
| Species | | | | |
| Soybean | 100 | 100 | 100 | 100 |
| Wheat | 40 | 40 | 40 | 90 |
| Corn | 30 | 20 | 30 | 95 |
| Velvetleaf | 100 | 100 | 100 | 100 |
| Morningglory | 100 | 100 | 100 | 100 |
| Chickweed | 100 | 100 | 100 | 100 |
| Cocklebur | 60 | 60 | 50 | 80 |
| Blackgrass | 40 | 60 | 50 | 100 |
| Green foxtail | 100 | 100 | 100 | 100 |
| Johnsongrass | 80 | 70 | 60 | 100 |

| | Compound No. | | | |
|---|---|---|---|---|
| | 34 | 35 | 36 | 37 |
| | Rate(kg/ha) | | | |
| | 0.3 | 0.3 | 0.3 | 0.3 |
| Species | | | | |
| Soybean | 100 | 100 | 100 | 100 |
| Wheat | 50 | 60 | 50 | 70 |
| Corn | 50 | 60 | 60 | 90 |
| Velvetleaf | 100 | 100 | 100 | 100 |
| Morningglory | 100 | 100 | 100 | 100 |
| Chickweed | 95 | 100 | 100 | 100 |
| Cocklebur | 50 | 80 | 90 | 100 |
| Blackgrass | 50 | 50 | 60 | ND |
| Green foxtail | 100 | 100 | 100 | 100 |
| Johnsongrass | 80 | 75 | 80 | 100 |

| | Compound No. | | | |
|---|---|---|---|---|
| | 38 | 39 | 40 | 41 |
| | Rate(kg/ha) | | | |
| | 0.3 | 0.3 | 0.3 | 0.3 |
| Species | | | | |
| Soybean | 100 | 70 | 100 | 100 |
| Wheat | 70 | 50 | 40 | 60 |
| Corn | 80 | 40 | 60 | 80 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 100 | 100 | 100 |
| Blackgrass | ND | ND | ND | ND |
| Green foxtail | 100 | 100 | 100 | 100 |
| Johnsongrass | 95 | 90 | 80 | 95 |

| | Compound No. | | | |
|---|---|---|---|---|
| | 42 | 43 | 44 | 45 |
| | Rate(kg/ha) | | | |
| | 0.3 | 0.3 | 0.3 | 0.3 |
| Species | | | | |
| Soybean | 70 | 100 | 100 | 100 |
| Wheat | 50 | 65 | 50 | 80 |
| Corn | 60 | 50 | 70 | 100 |
| Velvetleaf | 100 | 100 | 100 | 100 |
| Morningglory | 100 | 100 | 100 | 100 |
| Chickweed | 100 | 100 | ND | 90 |
| Cocklebur | 80 | 85 | 100 | 95 |
| Blackgrass | ND | ND | ND | 100 |
| Green foxtail | 100 | 100 | 100 | 100 |
| Johnsongrass | 80 | 80 | 90 | 100 |

| | Compound No. | | | |
|---|---|---|---|---|
| | 46 | 47 | 48 | 49 |
| | Rate(kg/ha) | | | |
| | 0.3 | 0.3 | 0.3 | 0.3 |
| Species | | | | |
| Soybean | 100 | 100 | 40 | 70 |
| Wheat | 30 | 10 | 60 | 60 |
| Corn | 30 | 20 | 80 | 80 |
| Velvetleaf | 100 | 80 | 100 | 100 |
| Morningglory | 100 | 80 | 100 | 100 |
| Chickweed | 100 | 0 | 90 | 100 |
| Cocklebur | 40 | 80 | 85 | 95 |
| Blackgrass | 50 | ND | ND | ND |
| Green foxtail | 100 | 100 | 100 | 100 |
| Johnsongrass | 70 | 80 | 75 | 85 |

| | Compound No. | | | |
|---|---|---|---|---|
| | 50 | 51 | 52 | 53 |
| | Rate(kg/ha) | | | |
| | 0.3 | 0.3 | 0.3 | 0.3 |
| Species | | | | |
| Soybean | 70 | 100 | 100 | 100 |
| Wheat | 80 | 90 | 70 | 90 |
| Corn | 70 | 100 | 95 | 90 |
| Velvetleaf | 100 | 100 | 100 | 100 |
| Morningglory | 100 | 100 | 100 | 100 |
| Chickweed | 100 | 100 | 100 | 100 |
| Cocklebur | 95 | 100 | 100 | 100 |
| Blackgrass | ND | 100 | 95 | 80 |
| Green foxtail | 100 | 100 | 100 | 100 |
| Johnsongrass | 80 | 100 | 100 | 100 |

| | Compound No. | | | |
|---|---|---|---|---|
| | 55 | 56 | 58 | 62 |
| | Rate(kg/ha) | | | |
| | 0.3 | 0.3 | 0.3 | 0.3 |
| Species | | | | |
| Soybean | 20 | 100 | 100 | 100 |
| Wheat | 65 | 80 | 100 | 85 |
| Corn | 75 | 90 | 95 | 100 |
| Velvetleaf | 90 | 100 | 100 | 100 |
| Morningglory | 75 | 100 | 100 | 100 |
| Chickweed | 90 | 100 | 100 | 100 |
| Cocklebur | 50 | 100 | 100 | 100 |
| Blackgrass | 50 | 80 | 100 | 95 |
| Green foxtail | 95 | 100 | 100 | 100 |
| Johnsongrass | 70 | 90 | 100 | 100 |

TABLE 3-continued

PREEMERGENCE HERBICIDAL ACTIVITY (% CONTROL)

| | Compound No. | | | |
|---|---|---|---|---|
| | 66 | 67 | 68 | 69 |
| | Rate(kg/ha) | | | |
| | 0.1 | 0.1 | 0.3 | 0.3 |
| Species | | | | |
| Soybean | 100 | 100 | 100 | 100 |
| Wheat | 95 | 90 | 90 | 95 |
| Corn | 100 | 95 | 95 | 100 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 100 | 100 | 100 |
| Blackgrass | 95 | 100 | 95 | 100 |
| Green foxtail | 100 | 100 | 100 | 100 |
| Johnsongrass | 100 | 100 | 95 | 100 |

| | Compound No. | | |
|---|---|---|---|
| | 70 | 93 | 124 |
| | Rate(kg/ha) | | |
| | 0.3 | 0.3 | 0.3 |
| Species | | | |
| Soybean | 100 | 100 | 100 |
| Wheat | 80 | 100 | 65 |
| Corn | 100 | 100 | 80 |
| Velvetleaf | 100 | 100 | 100 |
| Morningglory | 100 | 100 | 100 |
| Chickweed | 100 | 100 | 100 |
| Cocklebur | 100 | 100 | 100 |
| Blackgrass | 95 | ND | 95 |
| Green foxtail | 100 | 100 | 100 |
| Johnsongrass | 100 | 100 | 90 |

*= Average of two results
ND = no data

TABLE 4

POSTEMERGENCE HERBICIDAL ACTIVITY (% CONTROL)

| | Compound No. | | | |
|---|---|---|---|---|
| | 1 | 2 | 3 | 4 |
| | Rate(kg/ha) | | | |
| | 0.3 | 0.3 | 0.3 | 0.3 |
| Species | | | | |
| Soybean | 100 | 100* | 100 | 100 |
| Wheat | 100 | 80* | 100 | 100 |
| Corn | 100 | 100* | 100 | 100 |
| Velvetleaf | 100 | 100* | 100 | 100 |
| Morningglory | 100 | 100* | 100 | 100 |
| Chickweed | 100 | 100 | 100 | 100 |
| Cocklebur | 100 | 100* | 100 | 100 |
| Blackgrass | 100 | 92* | 100 | 100 |
| Green foxtail | 100 | 100* | 100 | 100 |
| Johnsongrass | 100 | 100* | 100 | 100 |

TABLE 4-continued

POSTEMERGENCE HERBICIDAL ACTIVITY (% CONTROL)

| | Compound No. | | | |
|---|---|---|---|---|
| | 5 | 6 | 7 | 8 |
| | Rate(kg/ha) | | | |
| | 0.3 | 0.3 | 0.3 | 0.3 |
| Species | | | | |
| Soybean | 100 | 100 | 80 | 90 |
| Wheat | 100 | 95 | 50 | 85 |
| Corn | 100 | 100 | 70 | 85 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 100 | 100 | 100 |
| Blackgrass | ND | ND | 60 | 70 |
| Green foxtail | 100 | 100 | 100 | 100 |
| Johnsongrass | 100 | 100 | 100 | 100 |

| | Compound No. | | | |
|---|---|---|---|---|
| | 9 | 10 | 11 | 12 |
| | Rate(kg/ha) | | | |
| | 0.3 | 0.3 | 0.3 | 0.3 |
| Species | | | | |
| Soybean | 90 | 70 | 60 | 100 |
| Wheat | 50 | 20 | 40 | 100 |
| Corn | 100 | 90 | 60 | 100 |
| Velvetleaf | 100 | 100 | 100 | 100 |
| Morningglory | 100 | 100 | 100 | 100 |
| Chickweed | 100 | 0 | 100 | ND |
| Cocklebur | 100 | 100 | 100 | 100 |
| Blackgrass | 100 | 0 | 10 | ND |
| Green foxtail | 100 | 100 | 100 | 100 |
| Johnsongrass | 100 | 95 | 50 | 100 |

| | Compound No. | | | |
|---|---|---|---|---|
| | 13 | 14 | 15 | 16 |
| | Rate(kg/ha) | | | |
| | 0.3 | 0.3 | 0.3 | 0.3 |
| Species | | | | |
| Soybean | 95 | 95 | 90 | 95 |
| Wheat | 90 | 50 | 70 | 70 |
| Corn | 95 | 90 | 95 | 60 |
| Velvetleaf | 100 | 100 | 100 | 100 |
| Morningglory | 100 | 100 | 100 | 100 |
| Chickweed | 100 | 100 | 100 | ND |
| Cocklebur | 100 | 100 | 100 | 90 |
| Blackgrass | ND | 50 | 100 | 70 |
| Green foxtail | 100 | 100 | 100 | 100 |
| Johnsongrass | 100 | 100 | 100 | 95 |

| | Compound No. | | | |
|---|---|---|---|---|
| | 17 | 18 | 19 | 20 |
| | Rate(kg/ha) | | | |
| | 0.3 | 0.3 | 0.3 | 0.3 |
| Species | | | | |
| Soybean | 90 | 30 | 90 | 100 |
| Wheat | 100 | 40 | 90 | 100 |
| Corn | 100 | 10 | 100 | 100 |
| Velvetleaf | 100 | 100 | 100 | 100 |

TABLE 4-continued

POSTEMERGENCE HERBICIDAL ACTIVITY (% CONTROL)

| | | | | |
|---|---|---|---|---|
| Morningglory | 90 | 80 | 100 | 100 |
| Chickweed | 100 | 100 | 100 | 100 |
| Cocklebur | 90 | 20 | ND | 100 |
| Blackgrass | 95 | 0 | 100 | 100 |
| Green foxtail | 100 | 40 | 100 | 100 |
| Johnsongrass | 100 | 50 | 100 | 100 |

| | Compound No. | | | |
|---|---|---|---|---|
| | 21 | 22 | 23 | 24 |
| | Rate(kg/ha) | | | |
| | 0.3 | 0.3 | 0.3 | 0.3 |
| Species | | | | |
| Soybean | 95 | 90 | 100 | 95 |
| Wheat | 50 | 40 | 100 | 70 |
| Corn | 65 | 70 | 100 | 100 |
| Velvetleaf | 100 | 100 | 100 | 100 |
| Morningglory | 100 | 100 | 100 | 100 |
| Chickweed | 90 | 85 | 100 | 100 |
| Cocklebur | 80 | 100 | 100 | 100 |
| Blackgrass | 50 | 60 | 100 | 90 |
| Green foxtail | 100 | 100 | 100 | 100 |
| Johnsongrass | 90 | 80 | 100 | 100 |

| | Compound No. | | | |
|---|---|---|---|---|
| | 25 | 26 | 27 | 28 |
| | Rate(kg/ha) | | | |
| | 0.3 | 0.3 | 0.3 | 0.3 |
| Species | | | | |
| Soybean | 95 | 95 | 100 | 95 |
| Wheat | 70 | 40 | 100 | 65 |
| Corn | 80 | 95 | 100 | 80 |
| Velvetleaf | 100 | 100 | 100 | 100 |
| Morningglory | 100 | 100 | 100 | 100 |
| Chickweed | 55 | 100 | 100 | 60 |
| Cocklebur | 100 | 100 | 100 | 80 |
| Blackgrass | 80 | 70 | 100 | 75 |
| Green foxtail | 100 | 100 | 100 | 100 |
| Johnsongrass | 100 | 95 | 100 | 100 |

| | Compound No. | | | |
|---|---|---|---|---|
| | 29 | 30 | 31 | 32 |
| | Rate(kg/ha) | | | |
| | 0.3 | 0.3 | 0.3 | 0.3 |
| Species | | | | |
| Soybean | 95 | 100 | 95 | 95 |
| Wheat | 50 | 40 | 30 | 95 |
| Corn | 100 | 100 | 70 | 100 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 100 | 100 | 100 |
| Blackgrass | 80 | 70 | 60 | 100 |
| Green foxtail | 100 | 100 | 100 | 100 |
| Johnsongrass | 95 | 90 | 80 | 100 |

TABLE 4-continued

POSTEMERGENCE HERBICIDAL ACTIVITY (% CONTROL)

| | Compound No. | | | |
|---|---|---|---|---|
| | 34 | 35 | 36 | 37 |
| | Rate(kg/ha) | | | |
| | 0.3 | 0.3 | 0.3 | 0.3 |
| Species | | | | |
| Soybean | 95 | 95 | 95 | 95 |
| Wheat | 60 | 55 | 60 | 95 |
| Corn | 100 | 90 | 90 | 100 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 100 | 100 | 100 |
| Blackgrass | 60 | 80 | 70 | ND |
| Green foxtail | 100 | 100 | 100 | 100 |
| Johnsongrass | 80 | 80 | 80 | 100 |

| | Compound No. | | | |
|---|---|---|---|---|
| | 38 | 39 | 40 | 41 |
| | Rate(kg/ha) | | | |
| | 0.3 | 0.3 | 0.3 | 0.3 |
| Species | | | | |
| Soybean | 95 | 100 | 100 | 90 |
| Wheat | 60 | 60 | 45 | 80 |
| Corn | 100 | 80 | 90 | 100 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 100 | 100 | 80 |
| Blackgrass | ND | ND | ND | ND |
| Green foxtail | 100 | 100 | 100 | 100 |
| Johnsongrass | 90 | 90 | 80 | 100 |

| | Compound No. | | | |
|---|---|---|---|---|
| | 42 | 43 | 44 | 45 |
| | Rate(kg/ha) | | | |
| | 0.3 | 0.3 | 0.3 | 0.3 |
| Species | | | | |
| Soybean | 95 | 95 | 95 | 95 |
| Wheat | 50 | 50 | 40 | 70 |
| Corn | 90 | 80 | 60 | 80 |
| Velvetleaf | 100 | 100 | 100 | 100 |
| Morningglory | 100 | 100 | 100 | 100 |
| Chickweed | 100 | 100 | 100 | 70 |
| Cocklebur | 100 | 100 | 100 | 70 |
| Blackgrass | ND | ND | ND | 70 |
| Green foxtail | 100 | 100 | 100 | 100 |
| Johnsongrass | 100 | 95 | 50 | 100 |

| | Compound No. | | | |
|---|---|---|---|---|
| | 46 | 47 | 48 | 49 |
| | Rate(kg/ha) | | | |
| | 0.3 | 0.3 | 0.3 | 0.3 |
| Species | | | | |
| Soybean | 80 | 95 | 90 | 80 |
| Wheat | 40 | 40 | 50 | 50 |
| Corn | 90 | 95 | 80 | 75 |
| Velvetleaf | 100 | 100 | 100 | 100 |

TABLE 4-continued

POSTEMERGENCE HERBICIDAL ACTIVITY (% CONTROL)

| Species | | | | |
|---|---|---|---|---|
| Morningglory | 100 | 100 | 100 | 100 |
| Chickweed | 100 | ND | 80 | 75 |
| Cocklebur | 100 | 100 | 100 | 95 |
| Blackgrass | 50 | ND | ND | ND |
| Green foxtail | 100 | 100 | 100 | 100 |
| Johnsongrass | 70 | 70 | 100 | 90 |

| | Compound No. | | | |
|---|---|---|---|---|
| | 50 | 51 | 52 | 53 |
| | Rate(kg/ha) | | | |
| | 0.3 | 0.3 | 0.3 | 0.3 |
| Species | | | | |
| Soybean | 85 | 95 | 95 | 100 |
| Wheat | 70 | 80 | 70 | 100 |
| Corn | 90 | 90 | 95 | 90 |
| Velvetleaf | 100 | 100 | 100 | 100 |
| Morningglory | 80 | 100 | 100 | 100 |
| Chickweed | 100 | 100 | 100 | 100 |
| Cocklebur | 80 | 100 | 100 | 100 |
| Blackgrass | ND | 100 | 100 | 100 |
| Green foxtail | 100 | 100 | 100 | 100 |
| Johnsongrass | 100 | 100 | 100 | 100 |

| | Compound No. | | | |
|---|---|---|---|---|
| | 55 | 56 | 58 | 62 |
| | Rate(kg/ha) | | | |
| | 0.3 | 0.3 | 0.3 | 0.3 |
| Species | | | | |
| Soybean | 70 | 95 | 100 | 100 |
| Wheat | 30 | 50 | 100 | 100 |
| Corn | 70 | 70 | 100 | 100 |
| Velvetleaf | 100 | 100 | 100 | 100 |
| Morningglory | 100 | 100 | 100 | 100 |
| Chickweed | 80 | 80 | 100 | 100 |
| Cocklebur | 100 | 100 | 100 | 100 |
| Blackgrass | 40 | 60 | 100 | 100 |
| Green foxtail | 100 | 75 | 100 | 100 |
| Johnsongrass | 75 | 80 | 100 | 100 |

| | Compound No. | | | |
|---|---|---|---|---|
| | 66 | 67 | 68 | 69 |
| | Rate(kg/ha) | | | |
| | 0.1 | 0.1 | 0.3 | 0.3 |
| Species | | | | |
| Soybean | 100 | 100 | 95 | 100 |
| Wheat | 100 | 100 | 100 | 100 |
| Corn | 100 | 100 | 100 | 100 |
| Velvetleaf | 100 | 100 | 100 | 100 |
| Morningglory | 100 | 100 | 100 | 100 |
| Chickweed | 100 | 100 | 100 | 100 |
| Cocklebur | 100 | 100 | 100 | 100 |
| Blackgrass | 100 | 100 | 100 | 100 |
| Green foxtail | 100 | 100 | 100 | 100 |
| Johnsongrass | 100 | 100 | 100 | 100 |

POSTEMERGENCE HERBICIDAL ACTIVITY (% CONTROL)

| | Compound No. | | |
|---|---|---|---|
| | 70 | 93 | 124 |
| | Rate(kg/ha) | | |
| | 0.3 | 0.3 | 0.3 |
| Species | | | |
| Soybean | 100 | 100 | 95 |
| Wheat | 90 | 100 | 55 |
| Corn | 100 | 100 | 100 |
| Velvetleaf | 100 | 100 | 100 |
| Morningglory | 100 | 100 | 100 |
| Chickweed | 100 | 100 | 100 |
| Cocklebur | 100 | 100 | 100 |
| Blackgrass | 90 | ND | 90 |
| Green foxtail | 100 | 100 | 100 |
| Johnsongrass | 100 | 100 | 100 |

*= Average of two results
ND = no data

We claim:

1. A compound of the formula

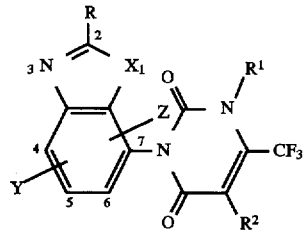

in which:

R is halogen, alkyl, alkenyl, alkynyl, phenyl, phenylalkyl, alkylphenylalkyl, haloalkyl, hydroxy, alkoxy, hydroxyalkyl, halophenyl, halophenylalkyl, alkoxyphenyl, sulfhydryl, alkylthio, piperidinyl, alkylamino, alkoxyalkyl, phenoxy, amino, alkylsulfonylamino, phenylsulfonylamino, carboxy, propionyl, halopropionyl, allyloxy, propargyloxy, acetylamino, alkylthienyl, alkoxyphenylalkyl, alkylsulfinyl, alkylsulfonyl, acetoxyalkyl, alkylcarbonyidioxyalkyl, alkylaminosulfonylamino, haloalkylsulfonylamino, phenylaminosulfonylamino, N-alkylsulfonyl-N-alkylamino, N-alkylsulfony-N-alkoxyalkylamino, N-alkylsulfonyl-N-alkynylamino, N-alkylsulfonyl-N-alkenylamino, N-phenylsulfonyl-N-alkylamino, acetoxyalkylamino, acetoxy, sodium carboxylato, aminocarboxylato, alkylcarbamoyl, alkylsulfonylcarbamoyl, alkoxycarbonyl, acetoxyhaloalkyl, acetoxyalkenyl, acetoxyhaloalkenyl, acetoxyalkoxy, alkenyloxy, alkynyloxy, acetoxyalkylthio, cyanoalkylthio, alkynylthio, phenylalkylthio, acetoxyalkylthioalkyl, phenylalkylthioalkyl, alkylsulfonylaminoalkyl, alkoxyphosphinyloxyamino, N-acetyl-N-alkylsulfonylamino, alkynyloxyalkyl, alkylcarboxylatophenoxy, halophenoxy, alkylphenoxy, alkoxypropionyloxyphenoxy, or haloalkoxypropionyl;

$R^1$ is alkyl or amino;

$R^2$ is hydrogen or halogen;

X is oxygen or sulfur;

Y is hydrogen, halogen, alkoxy, cyano, or nitro, and;

Z is halogen;

where halogen is bromine, chlorine, fluorine, or iodine, each alkyl, alkoxy, alkenyl, or alkynyl moiety, alone or in a combined term has one to six carbon atoms, and each phenyl moiety is optionally substituted with halogen, alkyl, or alkoxy.

2. A compound of claim 1 in which

R is alkyl, phenylalkyl, haloalkyl, hydroxyalkyl, sulfhydryl, alkylthio, piperidinyl, amino, alkylamino, or alkoxyalkyl;

$R^1$ is methyl or amino;

$R^2$ is hydrogen or chlorine;

Y is hydrogen, 4-chloro, 4-bromo, or 4-nitro;

Z is 6-chloro when Y is hydrogen or 6-fluoro when Y is other than hydrogen; and each alkyl moiety has one to four carbon atoms.

3. A compound of claim 2 in which R is alkyl, haloalkyl, hydroxyalkyl, sulfhydryl, alkylthio, alkoxyalkyl, or benzyl, optionally ring-substituted with chlorine or alkoxy; $R^1$ is methyl; $R^2$ is hydrogen; X is oxygen; Y is 4-chloro; and Z is 6-fluoro.

4. A compound of claim 3 in which R is alkyl, dibromomethyl, hydroxyalkyl, sulfhydryl, alkylthio, methoxymethyl, or benzyl ring-substituted with chlorine or methoxy.

5. The compound of claim 4 in which R is t-butyl.

6. The compound of claim 4 in which R is methyl.

7. The compound of claim 4 in which R is methoxymethyl.

8. The compound of claim 4 in which R is 3-methoxybenzyl.

9. The compound of claim 4 in which R is amino.

10. The compound of claim 4 in which R is 1-hydroxy-1-methylethyl.

11. The compound of claim 4 in which R is 2-hydroxy-1,1-dimethylethyl.

12. The compound of claim 4 in which R is dibromomethyl.

13. The compound of claim 4 in which R is sulfhydryl.

14. The compound of claim 4 in which R is methylthio.

15. The compound of claim 4 in which R is ethylthio.

16. A herbicidal composition comprising an herbicidally effective amount of a compound of claim 1 in admixture with an agriculturally acceptable carrier.

17. The method of controlling undesired plant growth which comprises applying to the locus where control is desired a herbicidally effective amount of a composition of claim 16.

18. A compound of the formula

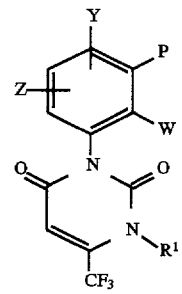

in which:

P is nitro, amino, or azido;

W is hydrogen, alkoxy, or hydroxy;

$R^1$ is hydrogen, alkyl, or amino;

X is oxygen;

Y is hydrogen, hydrogen, halogen, alkoxy, or nitro;

Z is halogen;

where each alkyl or alkoxy has one to six carbon atoms:

and P and W together may be —N—C(O)—O— to complete a benzoxazolinone ring.

19. The compound of claim 18 which is 3-(2-oxo-4-chloro-6-fluoro-2,3-dihydrobenzoxazol-7-yl)-1-methyl-6-trifluoromethyl-2,4-(1H,3H)pyrimidinedione.

* * * * *